(12) United States Patent
Lina

(10) Patent No.: US 6,468,237 B1
(45) Date of Patent: *Oct. 22, 2002

(54) PNEUMATIC PUMP, HOUSING AND METHODS FOR MEDICAL PURPOSES

(75) Inventor: Cesar Z. Lina, Universal City, TX (US)

(73) Assignee: Kinetic Concepts, Inc., San Antonio, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 100 days.

(21) Appl. No.: 08/847,321

(22) Filed: Apr. 23, 1997

Related U.S. Application Data

(63) Continuation of application No. 08/651,619, filed on May 22, 1996, now abandoned, which is a continuation of application No. 08/534,184, filed on Sep. 26, 1995, now abandoned, which is a continuation of application No. 08/422,637, filed on Apr. 14, 1995, now abandoned, which is a continuation of application No. 08/280,774, filed on Jul. 26, 1994, now abandoned, which is a continuation of application No. 08/039,574, filed on Mar. 25, 1993, now abandoned, which is a continuation-in-part of application No. 07/809,423, filed on Dec. 17, 1991, now abandoned.

(51) Int. Cl.$^7$ ................................................ A61H 7/00
(52) U.S. Cl. ..................................... 601/150; 601/151
(58) Field of Search ........................... 601/27, 84, 104, 601/148–156; 602/27, 23, 202

(56) References Cited

U.S. PATENT DOCUMENTS

| | | | | |
|---|---|---|---|---|
| 3,618,595 A | * | 11/1971 | Stahmer | 128/25 R |
| 4,106,002 A | * | 8/1978 | Hogue, Jr. | 606/202 |
| 5,027,797 A | * | 7/1991 | Bullard | 601/152 |

OTHER PUBLICATIONS

The Therapy Proven With Every Footstep—PlexiPulse™ brochure NuTech—A KCI Company (date unknown, but brochure bears 1991 copyright date).

\* cited by examiner

Primary Examiner—John P. Leubecker
(74) Attorney, Agent, or Firm—Mark R. Wisner

(57) ABSTRACT

A multi-faceted pneumatic medical device including a pump unit, together with a housing therefor, that is adapted for cyclical compression of the human foot using an expandable fluid-tight bladder formed integral within a wrap that can be securely fastened onto the foot.

14 Claims, 14 Drawing Sheets

PNEUMATIC PUMP, HOUSING AND METHODS FOR MEDICAL PURPOSES

RELATED APPLICATIONS

This application is a continuation of application Ser. No. 08/651,619 filed May 22, 1996, now abandoned, which is a continuation of application Ser. No. 08/534,184 filed Sep. 26, 1995, now abandoned, which is a continuation of application Ser. No. 08/422,637 filed Apr. 14, 1995, now abandoned, which is a continuation of application Ser. No. 08/280,774 filed Jul. 26, 1994, now abandoned, which is a continuation of application Ser. No. 08/039,574 filed Mar. 25, 1993, now abandoned, which is a continuation-in-part application Ser. No. 07/809,423 filed Dec. 17, 1991, now abandoned.

This is a continuation-in-part application which relates and claims priority to co-pending U.S. patent application Ser. No. 07/809,423, filed Dec. 17, 1991, entitled "Pneumatic Pump, Housing and Methods for Medical Purposes," for which Cesar Z. Lina and Randall L. Ohman are listed inventors (the "Co-Pending Application"). The specification of said Co-Pending Application, along with its drawings and any other information appended thereto or incorporated therein, are incorporated in this present application by this reference as though set forth here in its entirety.

BACKGROUND OF THE INVENTION

1. Field of the Invention

The present invention relates generally to a method and apparatus for cyclic compression of a body's extremities, as well as a related system with a housing for containing and mounting the device on the foot board of a hospital bed.

2. Related Art

Medical devices that apply cyclic pressure to a person's legs, arms, hands and/or feet are very old and well-known in the art. Many have employed pulsating pads, pistons and plungers for improving circulation. Others have used hydraulic and pneumatic bladders for similar purposes. The shapes, sizes, and composition of such bladders, pads and the like are widely varied, depending largely on their particular application.

Man has known the fundamental principle of most cyclic compression devices for many years. They are merely a more recent embodiment of the old art of massage, which has probably been used to stimulate circulation for ages. Use of mechanical devices to effect the massaging action is obviously more recent, but has a clear history of over a century.

Full understanding of the mechanism involved in this form of improving blood flow is more recent but has not fundamentally changed the devices used to accomplish this result. Veins have long been known to contain a series of one-way check valves along their length. Thus, when pressure is applied, compressing a vein, the fluid expelled therefrom can only proceed in the direction of normal circulation. When such compression is relaxed, the vein returns to its normal circular cross-section and the flow of blood into the vein is increased until it reaches its normal state of back pressure. Repeating this cycle in a cyclic fashion thus increases blood flow in the normal direction of circulation.

Such compression decompression cycles occur naturally in humans as part of the action of the muscles and flexure of the limbs. It has been known for many decades that the foot includes a large venous plexus (or group of veins). It is also known that this venous plexus is compressed during normal walking or running, thereby stimulating circulation. This efficient circulation aid is a marvelous design by our Creator, as its effect is greatest when the leg muscles (the largest muscles in the body) are in action and need the oxygen supplied by enhanced circulation.

For these and other reasons, the foot has long been known as an effective site for applying cyclic pressure. For instance, many devices such as Massator's "PediPulsor" improve circulation by positioning a pulsating, dome-shaped pad in the arch of the foot. Many others have targeted the arch of the foot with flexible pneumatic chambers. A partial sampling of such pneumatic devices that target the arch of the foot are described in the masters thesis of James C. W. Parrott, B. Sc., B. Sc. (Med.), M.D., entitled *The Effect Of A Mechanical Venous Pump On The Circulation In The Feet In The Presence Of Arterial Obstruction*, and dated October, 1992 and found in the University of Manitoba library and includes Japanese Utility Model No. 72-10392, U.S. Pat. No. 4,614,180 in the name of Gardner and Fox, and U.S. Pat. No. 4,941,458 in the name of Taheri.

Many others have long recognized that the foot contains veins that can be massaged or pumped to provide better circulation. Some examples are: U.S. Pat. Nos. 3,824,992 and 3,901,221 to Nicholson, et al; Richard Dillon M.D. whose *Journal of Vascular Diseases*, January 1986 report on treatment of circulation-impaired patients states "compression boot therapy enjoys a 173 year history;" and P. Gaskell M.D. and J. C. W. Parrott M.D. whose *Surgery, Gynecology, and Obstetrics*, April 1978 report, which is a summary of Dr. Parrott's Master's Thesis, documented an early demonstration of the process of venous pumping with pulsed air by stating "We have found that the boot covering the foot alone is simpler, less cumbersome, and gives a greater reduction of venous pressure than either a large cuff which covers the whole calf or a boot which includes the calf and the foot."

Such devices and many other medical devices are typically auxiliary devices which may or may not be employed on each patient. Because of their auxiliary nature, it is beneficial for such devices to be compact, portable and easily employed and stored adjacent a hospital bed. Other devices have addressed such concerns with hooks that allow the device to be hung on the foot board of a bed. However, because of the wide range of foot board sizes that must be accommodated, such hooks either have to be customized for certain foot boards, or else the snugness and security of the fit must be compromised. Further background and many other related references are known to those of skill in this art.

Despite the long history of technological developments of such housings and compression devices, man continues in his manifest pursuit of the ideal system which balances maximum therapeutic benefit with practicality and patient comfort.

Many other problems, obstacles and deficiencies faced in these fields and/or addressed by the present invention will be apparent to those skilled in that art, especially in light of the further descriptions herein.

SUMMARY OF THE INVENTION

It is a primary object of the present invention to provide a new and improved cyclic compression system which overcomes the problems and deficiencies of the prior art.

It is also an object of the present invention to provide a novel housing which can be conveniently handled and simply but securely mounted to a hospital bed or the like. Another object of the invention is to produce a simple, compact, inexpensive pump and housing which are capable of yielding substantial therapeutic and prophylactic benefits despite their small size and simplicity.

The present invention is directed toward accomplishing such objects and others and improving upon the teachings of the prior art by uniquely combining, refining and modifying various concepts and features to provide a significant advancement in the field. A primary object of the invention is to provide a small, lightweight and comfortable but durable device which helps prevent and/or solve many of the problems associated with impaired or poor circulation.

Another object includes providing a pneumatic device of simple construction which encloses as much of the foot as possible in order to squeeze as much of the foot as possible. Particularly it is an object to enclose those portions which may be readily compressed to improve circulation while allowing other less compressible portions to be open to the air. Still other objects include providing comfort and moisture control and avoiding the need for accessories such as additional stockings, wraps, sandals, straps, and the like, which have been required by the prior art.

Another object of the present invention is to provide an intermittent compression device requiring a minimum volume of air per pulsation.

Another object is to provide a blood circulation aid which will fit a wide variety of patients without requiring any modification or adjustments.

Another object of the present invention is to provide a disposable device of simple construction which is of a universal shape in that it can be applied to either the left or the right foot with the same effect.

Another object is to provide a device of great simplicity and ease-of-use in contrast to other devices designed for the purpose of aiding blood flow in the feet and legs. Related objects include providing a lightweight, simple article that can be easily and quickly applied to the foot while still achieving the other objects of the invention.

Another object of the invention is to provide a blood flow improvement device which, due to its inherent low manufacturing cost, is practical to use as a disposable item rather than cleaning and reusing.

Still another object is to provide a cyclic compression device which achieves optimum compression and optimum blood flow enhancement in a manner that minimizes anxiety and discomfort to the patient.

Other objects relate to the convenience of the product. It is desired to provide a complete system that can be hand carried to the patient and easily and securely deployed without concern about compatibility with the bed on which the product is to be deployed. A compact, easily-stored and minimally-obtrusive product is also sought.

The present invention addresses the foregoing and many other objects by providing an ingenious article that integrates a compression bladder and its entire mounting, stabilizing and adjustment systems into a simple and economical construction coupled with a control system and housing that greatly surpass prior devices both in utility and ingenuity.

The present invention will typically comprise a foot wrap device made from two sheets of fabric sewn or welded together to form an inflatable pocket or bladder that preferably constitutes as much of the device as possible without creating a bladder that is too uncomfortable or too large to be adequately inflated. One aspect of the invention relates to the roughly T-shaped or L-shaped configuration of its foot wrap, with at least one portion or segment wrapping around the bottom of the foot and a second portion or segment wrapping around the back of the heel and ankle regions of the lower leg. As will be described with reference to the preferred embodiments, the invention may include various extensions or tabs provided to operatively join with other extensions, tabs or the like, as may be beneficial for comfort and efficacy. In the preferred embodiments, both inner and outer fabric layers are cut from the same pattern.

Fasteners formed integral with the extensions enable releasable application on the foot. Preferably, such fasteners include Velcro hook connectors, and the outer surface of the foot wrap is formed of Velcro loop material (or the equivalent) for mating with the hook connectors. The inner layer of the foot wrap is preferably a vapor permeable material having greater elasticity than the outer layer. Both fabrics are preferably impermeable to air and capable of being fused together by heat welding or the like. A filling tube may be sealed into the inflatable bladder or pocket through the outer fabric layer.

In the first embodiment, the complete foot wrap weighs only a few ounces and is soft and pliable. When it is properly applied, a first dimpled or segmented portion of the inflatable bladder wraps around the main part of the foot and fastens to itself. Another portion is joined integrally in fluid communication with the first but wraps around behind the heel and ankle regions of the lower leg. The second portion fastens to the outside surface of either itself or the other portion. Thus, the foot is almost completely enclosed and surrounded by the inflatable bladder, and the device securely holds itself in place on the foot in order to compress as much of the foot as feasible when the bladder is inflated.

Fluid for such inflation may be supplied by one of the pump systems well known in the art, although the preferred embodiment includes and provides several advancements over that art. The preferred embodiment includes a pump that operates in a pulsed sequence that can be adjusted for any desired frequency and intensity according to the prescribed treatment. Preferably the pump/control is set to compress the foot to pressures in the range between 120 and 190 mm Hg and to hold it in that pressure range for two seconds every fifteen seconds. This pressure range is generally accepted by Applicant to ensure closure of the veins in the foot, although lower pressures may be partially effective as well.

The preferred embodiments uniquely integrate more fundamental aspects of the invention together with cushioning means for minimizing localized pressure concentrations acting on the foot, thereby inhibiting skin breakdown on the foot, especially its most vulnerable areas. Optimum compression of the foot is ensured by enclosing as much of the squeezable portion of the foot as is feasible. In the first embodiment, the inner and outer sheets are joined together at circular portions in the interior of its inflatable bladder to help prevent excessive inflation, particularly over regions of the foot that are less compressible. This further optimizes compression of the foot to ensure optimum blood flow enhancement. Holes may be provided through the wrap at those circular portions to further enhance breathability of the patient's skin.

The present invention also includes a unique pressure source for supplying pressure to the referenced foot wraps. Pressure feedback control of the pressure supplied by the pressure source is provided even during the then-current compression cycle. The feedback system overcomes some of the difficulties inherent in its objects by incorporating spike eliminators, as well as error detection means for alarming the operator of error conditions such as kinked hoses or disconnected foot wraps. The spike eliminator may include an accumulator, possibly in combination with a flow restrictor. The accumulator and restrictor are configured in a way that helps prevent the pressure sensors from over-responding to initial surges of line pressure. Such surges are otherwise common close to the pressure source with compression devices that provide quick inflation.

More particularly, the pressure sensing and control system may include a transducer, an analog-to-digital converter, and a digital micro-controller that controls a plurality of solenoid valves to adjust the supplied pressure in accordance with operator settings. The micro-controller is interfaced through an operator console having a liquid crystal display and programmable keys to enter operator settings, which are then stored using various memory devices including electronically erasable programmable read only memory.

The combination of all the foregoing in an operative system is thought to be very beneficial, especially packaged in a housing that can be releasably mounted on the foot board of a standard hospital bed by means of a pair of opposite, retractable mounting hooks having sloped surfaces for biasing the source toward said foot board and having knobs at the distal ends thereof for helping retain the hooks on the foot board.

Numerous other features, advantages, and objects of the invention are set forth and will be evident from the following more detailed descriptions of certain preferred embodiments, particularly when considered in light of the prior art together with the accompanying drawings and appended claims.

BRIEF DESCRIPTION OF THE DRAWINGS

Presently preferred embodiments constructed according to the teachings of the present invention are hereinafter described in more detail. To those of ordinary skill in the art, the invention will become more readily understood from the specifications of those embodiments, particularly when considered in light of the appended claims and with further reference to the accompanying drawings, wherein like numerals refer to like elements throughout, and wherein:

FIG. 13 shows a top view of the preferred embodiment's pump housing 20, which also functions as a carrying case and as a means for mounting the pump on the foot board of a hospital bed or the like.

DETAILED DESCRIPTION OF PREFERRED EMBODIMENTS

Figure 1:
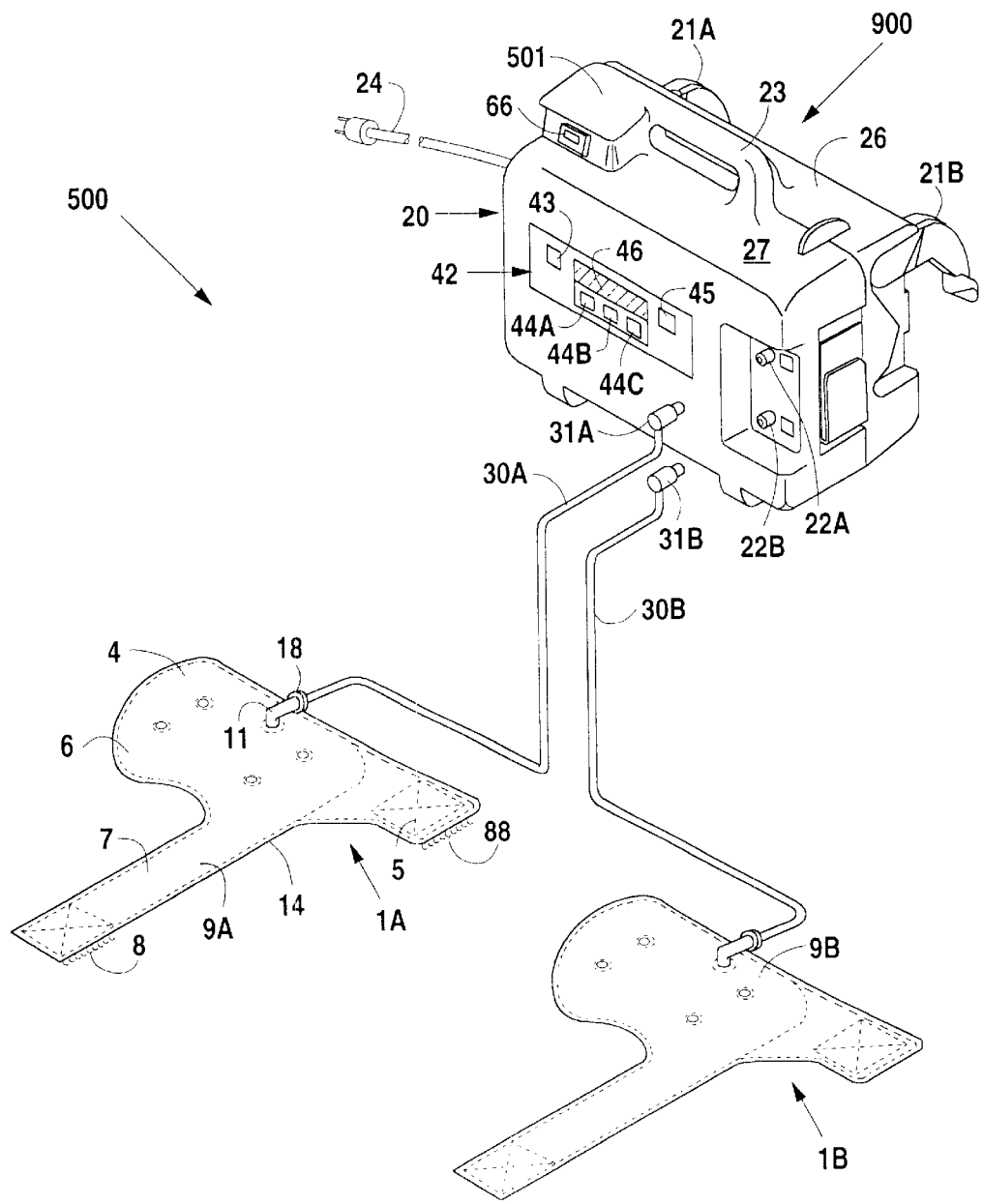
FIG. 1 shows a perspective view of the basic elements of one of the presently preferred embodiments.

Referring to FIG. 1 of the drawings, there is shown an isometric perspective view of the basic elements of the presently preferred embodiment. That embodiment, referred to as cyclic compression system 500, basically comprises a pump unit 501, two foot wraps 1A & 1B, power cord 24, and connecting hoses 30A and 30B. In many respects that embodiment is intended to be substantially identical to a product known in the marketplace as the "PlexiPulse" unit manufactured by Applicant Kinetic Concepts, Inc., San Antonio, Tx. The "PlexiPulse" unit is now available to customers of NuTech, which is affiliated with Kinetic Concepts, Inc., and also has offices in San Antonio, Tx. Although the following description is intended to be complete within itself and with reference to its corresponding Co-Pending Application (referred to previously), further reference to said PlexiPulse unit may further enable those of ordinary skill in the art to make and use the inventions hereof.

The pump unit 501, which is AC-powered via a conventional power cord 24, operates to cyclically inflate and deflate bladders 9A and 9B formed in foot wraps 1A and 1B, respectively, to intermittently compress the foot. The unit is described most particularly for application on the foot, as many aspects of the invention can be appreciated there. Nonetheless, regardless whether it is mounted on a patient's calf, foot, hand, or any other part of the body (especially those containing veins that can be emptied by compression), such intermittent compression may be beneficial for a wide variety of indications. Among others, the known medical indications include the following: venous stasis, poor circulation, post-operative pain and swelling, edema, cutaneous ulceration, and elevated compartmental pressures. It may also serve to prevent deep vein thrombosis and reduce wound healing times. More particular aspects of preferred operation of the system 500 will be described further herein.

For purposes of this description, reference may be made to "upper", "lower", "forward", "backward", "left", "right"

and "horizontal" features when referring to certain drawings. Such references and others like them are made principally to render the description more easily understood in view of the orientations in the drawings and in view of a reference orientation of system 500 or its subject. As will be evident to those of ordinary skill in the art, such orientations are not necessarily maintained throughout the operation of the described embodiments, much less would they necessarily be required for utilization of the invention.

Referring to FIGS. 2–7, foot wrap 1A is shown, first laid flat and then in relation to a foot (designated as foot 100 in the drawings) during normal operation. Foot wrap 1A is preferably identical to foot wrap 1B (shown in FIGS. 1 and 9) and thus has parts which are numbered the same as in the other figures, except that the "A" and "B" designations may be used to distinguish various parts of wrap 1A from similar parts of wrap 1B, respectively. Variations in the shape of foot wrap 1A may be made to some degree, with commensurate sacrifices in (or enhancement of) the benefits of the invention. The angle of the inlet 11 relative to the foot wrap 1A, for instance, may be varied from one foot wrap to the next without much effect on its operation. The inlet angle pictured in FIG. 1 is considered most advantageous, tending to bias hose 30A in a direction for avoiding kinking of that hose 30A. The descriptions of foot wrap 1A are equally applicable to foot wrap 1B. One aspect of the invention is that the shape of wrap 1A renders it universal in that it is thought to be applicable to either foot without significantly affecting its efficacy. As will be evident, though, the foot wrap 1B could be made as a mirror image of its counterpart 1A. The simplicity of the shape also allows for the wrap 1A to fit on other body portions as well even though it is ideally suited for the foot.

Figure 2:
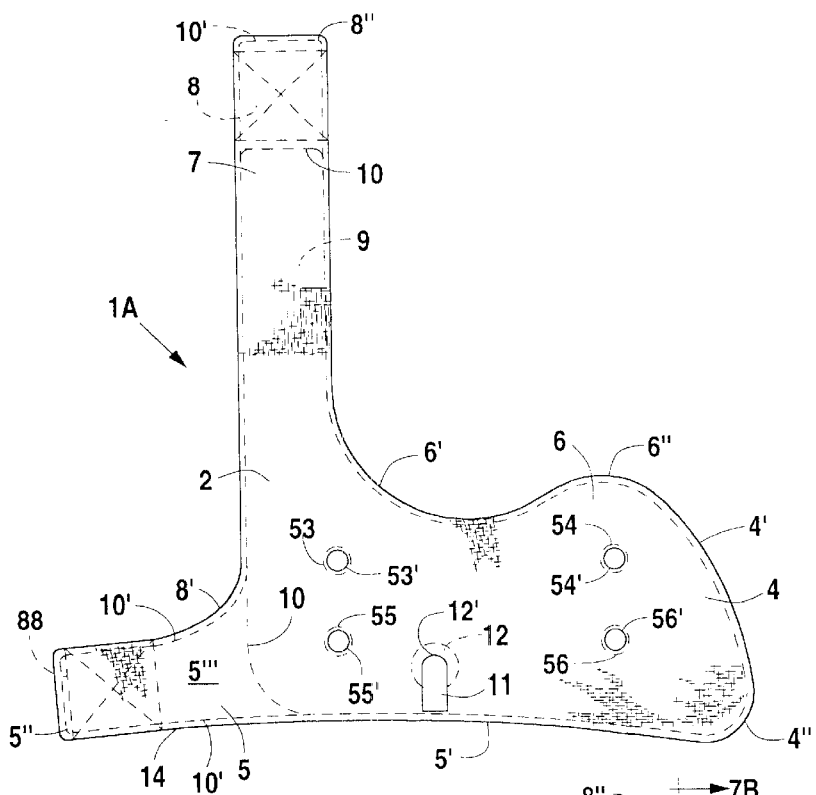
FIG. 2 shows the outer surface of one of the foot wraps 1A pictured in FIG. 1 as it is laid out flat.
Figure 3:
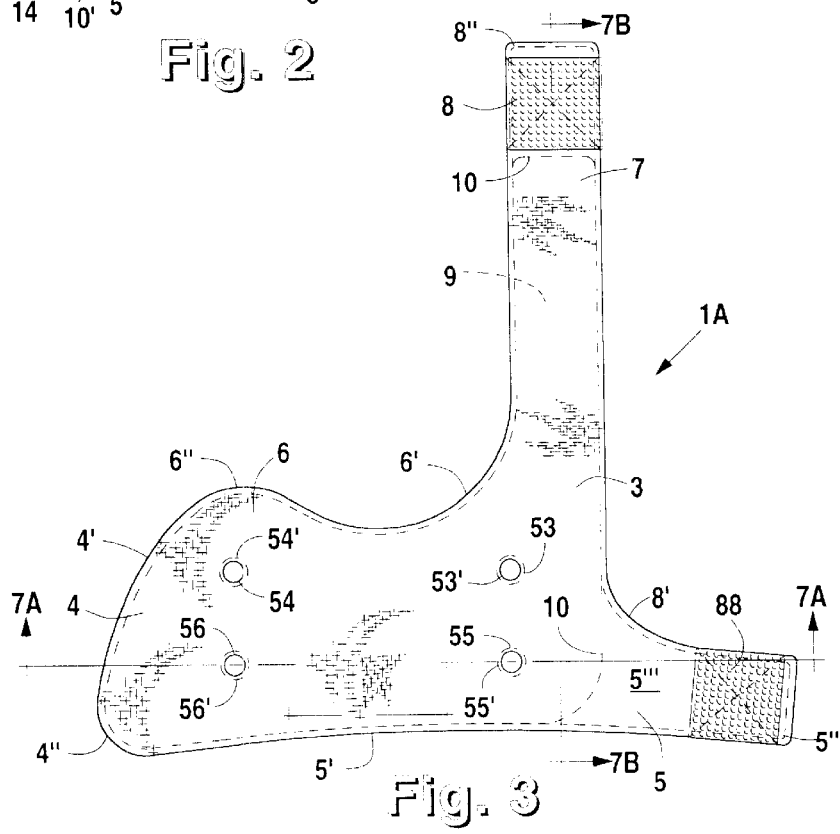
FIG. 3 shows a view of the inner surface of the foot wrap 1A laid flat.
Figure 6:
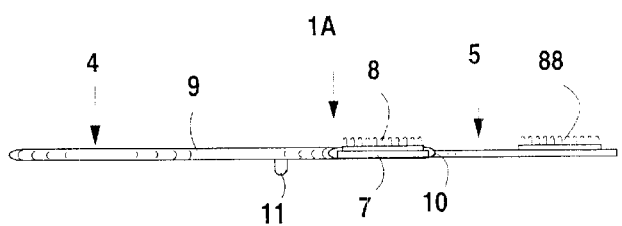
FIG. 6 shows an end-on view of the foot wrap 1A as it is laid out flat with its bladder 9 shown deflated, the view being from the end that is oriented at the top in FIG. 2.
Figure 7B:
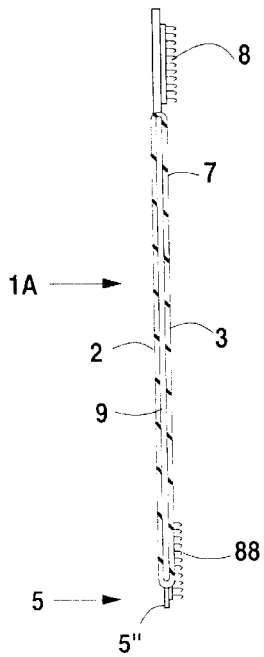
FIG. 7B shows a second cross-section of the foot wrap 1A, sectioned along plane "7B—7B" shown in FIG. 2, with its bladder 9 shown deflated.
Figure 7A:
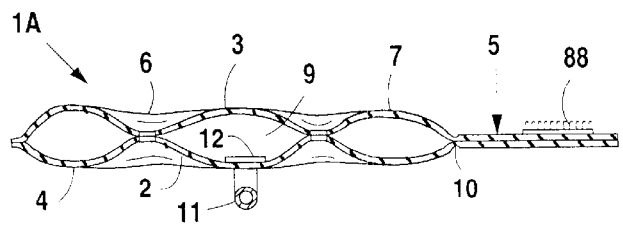
FIG. 7A shows a cross-sectional view from the opposite direction of FIG. 6, the section line "7A—7A" being shown in FIG. 3 and bladder 9 being shown inflated in FIG. 7A.

In FIG. 2, foot wrap 1A is shown open (i.e., laid out flat), with the outer surface of foot wrap 1A facing the viewer. FIG. 3 is a view from the opposite side showing the inner surface of foot wrap 1A. FIGS. 6–7B show various views that generally illustrate the construction of the foot wrap. The foot wrap 1A is generally formed of two sheets 2 and 3 which are bonded together to form a bladder 9 with tabs 4–7 extending generally away from each other. Foot wrap 1A also includes a fluid inlet 11 (also referred to as "fitting 11") for inflating and deflating the bladder 9, as well as fasteners 8 and 88 for releasably securing the wrap 1A on a foot 100. These basic components (and others) of wrap 1A are readily available through numerous manufacturers.

Referring primarily to FIG. 7B, sheet 2 is preferably cut from a robust, non-stretch fabric. The outer surface of sheet 2 (i.e., the surface facing away from sheet 3) has loops like those found on Velcro loop material, which are compatible to releasably engage Velcro hook material. The interior surface of sheet 2 (i.e., the surface facing toward sheet 3) is heat-weldable so that it can be joined to sheet 3. Sheet 2 is laminated with polyurethane in a conventional manner, to seal it and render it RF-weldable. Sheet 2, thus, is referred to as a sheet of laminated loop fabric that forms the outer sheet of wrap 1A. In the presently preferred embodiment, sheet 2 is a Velcro-compatible, continuous-loop nylon fabric manufactured by Guilford, USA and available under the trade designation "Tricot".

Preferably, although each of the sheets 2 and 3 are air impermeable, they are each also formed of vapor permeable fabric. Other commercially-available fabrics, such as that marketed as low air loss "GoreTex" by the W. L. Gore Company, have long been known to provide similar benefits in other contexts. Their vapor-permeability serves to enable moisture from foot 100 to evaporate despite the foot wrap 1A. This is especially preferable for sheet 3 so that perspiration adjacent bladder 9 can be evacuated from the site by the fluid that inflates bladder 9. The removal of surface moisture forming on the patient's skin beneath the foot wrap is beneficial since it helps promote the maintenance and healing of skin conditions, especially during prolonged use. As will be evident to those skilled in the art, however, some aspects of this invention can still be appreciated with materials of more limited porosity, generally so long as foot wraps 1A and 1B remain inflatable.

Sheet 3 is preferably cut from the same or a similar pattern as sheet 2, so that it matches neatly with sheet 2. The manufacturing process may be simplified by simultaneously die-cutting the sheets 2 and 3, and then joining the border and appropriate other locations of each sheet to the other (as described elsewhere herein). The cutting process may also be simplified by welding the two sheets together while simultaneously heat-cutting the border of the fabric with the same die (as is common in the art with tear-and-seal dies), although this process may not always be successful due to the compositions of the sheets.

Sheet 3 is preferably also an elastic fabric, so that it expands more than outer sheet 2 when bladder 9 is inflated. The inner surface of sheet 3 (i.e., the surface facing toward sheet 2) is laminated with polyurethane, thereby sealing it and rendering it heat-weldable to enable bonding with the inner surface of sheet 2. It is important that the outer surface of sheet 3 (i.e., the surface facing away from sheet 2) is soft and comfortable against the skin, as that surface is likely to be in contact with the patient's skin during use. In the preferred embodiment, sheet 3 is a laminated lycra material that meets the foregoing characteristics.

As will be evident from this description to those of ordinary skill in the art, other fabrics may be substituted for the preferred fabrics of sheets 2 and 3 with related sacrifices of various aspects of this invention. Less costly, substantially inelastic nylon fabrics could be used for both sheets 2 and 3 while still appreciating therapeutic value of the foot wraps 1A and 1B. Similarly, stitching or adhesives could be used rather than the more beneficial RF welding, and some benefits could still be appreciated with a PVC-like composition made of sheets appropriately welded together.

Preferably, bladder 9 is formed between sheet 2 and sheet 3 by weld line 10. Weld line 10 is a closed line so that it completely surrounds and thereby defines a closed area on each of sheets 2 and 3. Thus, bladder 9 is a sealed, bladder, the only inlet or outlet of which is provided by the tubular connector fitting 11 (described below). Bladder 9 is provided in foot wrap 1A to apply pressure on the foot 100 when the wrap 1A is secured on the foot 100 and the bladder is then inflated. Bladder 9 is primarily intended for pneumatic inflation, although fluids other than air could be substituted by those of ordinary skill in the art. Although bladder 9 would be of minimum size and volume consistent with its object of exerting compression pressure on the foot while requiring a minimum volume of pressurized air per pulse (as achieved by bladder 509 shown in the alternative embodiment of FIG. 21), Applicant believes that similar pressures distributed over more of the foot provides a greater benefit for the patient. Thus, bladder 9 of foot wrap 1A extends over most of the entire surface area of wrap 1A to overlap and enclose as much of the portions of the foot which contain significant veins as is feasible. Although bladder 9 in the preferred embodiment may not compress the veins in the toes of most patients, it is of sufficient size to compress virtually all other regions of the foot, except the most distal portion of the heels, which are thought to contain few significant veins for compression purposes.

Figures 21, 22:
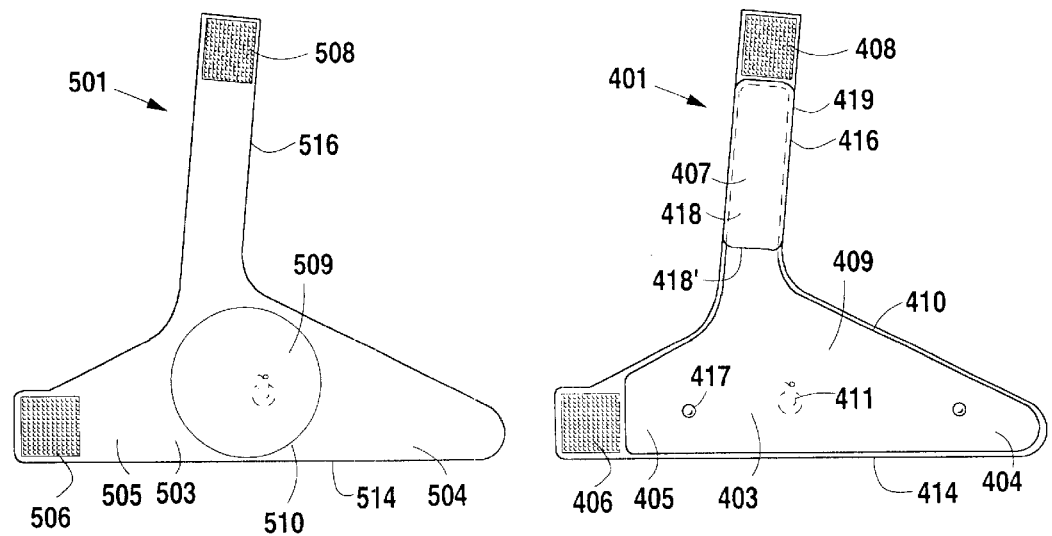
FIGS. 21–23 show alternative embodiments to the foot wrap 1A shown in FIG. 3.
Figure 23:
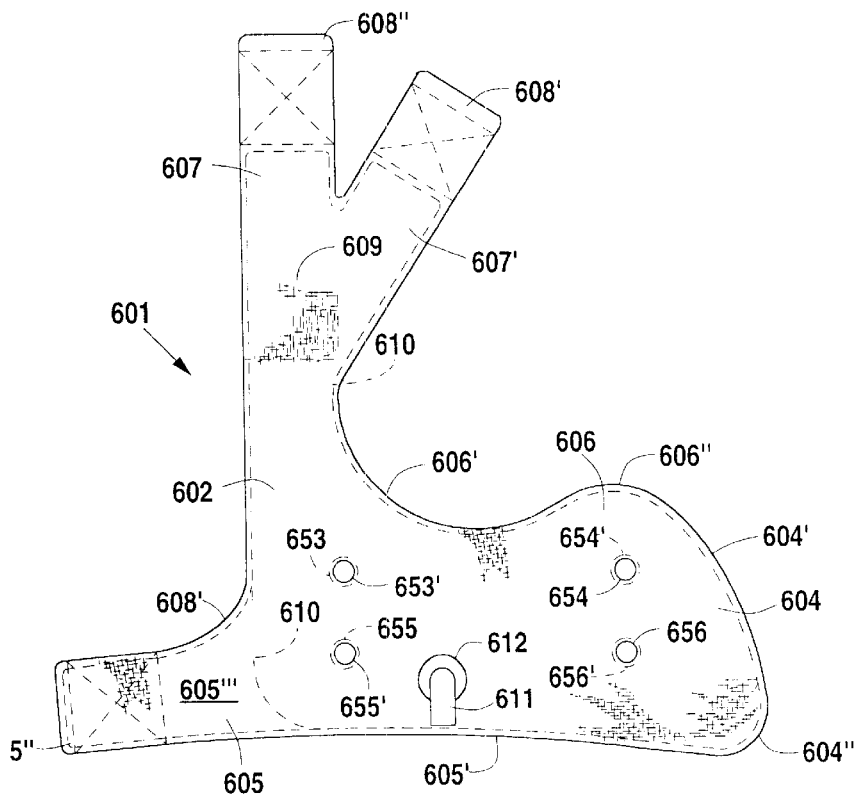

In contrast, it can be seen with reference to FIG. 21 that bladder 509 occupies only the central sole area of the foot 100. Pressure and bladder expansion there causes the fabric enclosure around the foot to tighten and distribute limited compression forces around other portions of the foot 100 as well. In the embodiment of FIG. 21, bladder 509 is circular, roughly 3 to 5 inches in diameter. However, other shapes of bladders may be substituted to employ many of the other aspects of the invention. For instance, FIGS. 22 and 23 show two other alternative embodiments to the foot wrap 1A shown in FIG. 3. FIG. 22, specifically, shows a T-shaped foot wrap 401 having a similarly T-shaped bladder 409 which is capable of enclosing much of foot 100, with some limitations. The differences between the shape of bladder 9 and bladder 409 ensure more complete enclosure of vein-containing portions by bladder 9, as well as enable its universal characteristics (referenced previously). In the opposite direction from the smaller shape of bladder 409 is bladder 609 shown in FIG. 23, which further ensures complete enclosure and compression of the vein-containing portions of foot 100, while also further ensuring a secure attachment to foot 100. Other variations and details are described in said Co-Pending Application and at least one other application referenced and incorporated therein.

Each of the embodiments shown in FIGS. 21–23 are constructed and used essentially using the same methods and materials as with the FIG. 3 embodiment, except as otherwise noted. Accordingly, like (or related) aspects of these various embodiments are numbered similarly. For instance, each embodiment has a strap that is positioned to be secured around the back of the leg of a person on which it is to be used. The respective straps are numbered 7, 507, 407 and 607, for FIGS. 3, 21, 22, and 23, respectively. The differences from the embodiment of FIG. 3 and those of FIGS. 21–23 will be fairly evident from a comparison of those figures.

The principal difference between the FIG. 3 embodiment and that of FIG. 21 relates to the size of the bladder. In attempts to render the wrap 1A more comfortable and more likely to ensure against skin breakdown, Applicant has found that by increasing the size of bladder 9 to that shown in FIG. 2, the resulting blood flow is improved. Although the findings are still preliminary, compressing more of the foot not only renders the wrap 9 more comfortable, but informal venogram studies indicate that greater surges of blood flow tend to be produced by compressing more of the foot. The same informal studies also suggest that the placement of circular welds 53–56 in the interior of bladder 9 further enhances blood flow. That cushioning effect is believed to help inhibit the breakdown of skin that might otherwise be associated with straps 507, 407 and 607—particularly breakdown created by stress concentrations on strap 407 and the skin around the rearward ankle area of foot 100. As is also true to some degree for the embodiment of FIG. 2, the embodiment shown in FIG. 22 is provided with means for cushioning the leg strap 407.

Wrap 401 achieves the cushion in part by having a foam strap 407 that is inherently cushioned and in part by extending its inflatable bladder along the length of the strap 507. Wrap 1A, in contrast, only achieves the cushion by extending its inflatable bladder 9 along the length of its strap 7. Foam strap 407 is an elongated patch of foam material that is secured to strap 407 in an orientation coincident with the length of strap 407. The cushion foam used in the preferred embodiments of the embodiments shown in FIGS. 21–23 is commercially available in the U.S. under the trademark "Vel-Foam", although other cushion material could also be used. Securing the foam 407 to the rest of foot wrap 401 may be accomplished either by a variety of conventional means, such as by stitching, glue, or heat-welded lamination. If stitching is to be used, the stitching is preferably done at a location of the wrap that is not inflatable, thereby avoiding leaks in the inflatable bladder. For instance, the Vel-Foam strap 407 is shown stitched on three sides to the remainder of wrap 401 with stitching 419 in a narrow region outside weld 410 that defines bladder 409. Vel-Foam patch 418 must be stitched around only three of its four edges (excluding edge 418') in order to avoid creating an air leak in bladder 409. Therefore it may be preferable to glue patch 418 in place using conventional glues used by seamstresses for lasting application.

Heat-welded circular recesses 417 are preferably spaced on bladder 409 to minimize billowing (excessive bulging) of bladder 409 when it is inflated. Such circular recesses are best positioned at locations likely to overly bonier (or less compressible) areas of foot 100.

Many other features of the embodiments shown in FIGS. 21–23 will be evident to those of ordinary skill in the art in view of the other teachings herein, and in view of the prior art.

The preferred shape of wrap 9 is unique and advantageous. Wrap 9 as a whole may be referred to as T-shaped, J-shaped or L-shaped depending on which elements are focused upon. For simplicity in reference, it will simply be referred to as a "convoluted J-shape". The convoluted J-shape of wrap 1A has four basic extensions referred to as tabs 4–7.

Tabs 4–7 are oriented to ideally secure wrap 1A to the foot 100 of the patient. As can be seen with reference to FIGS. 2–7, the heel edge 6' that spans between tab 6 and tab 7 is concave and has a generally circular curve for surrounding the heel 102 of foot 100. Once so wrapped to encircle the heel 102 of foot 100, Velcro connector 8 at the distal end of tab 7 is naturally oriented to overlap and secure itself to the outer surface of sheet 2 of tab 6. The toe edge 4' is also curved concavely, although only to a slight degree, to encircle the toe region 103 of the foot 100. Once so encircling the toe region of the foot, Velcro connector 88 overlaps and engages the outer surface of sheet 2 of tab 4. The size of Velcro tabs 8 and 88 should be determined based on the degree of closure desired, which is dependent, at least in part, upon the types of Velcro materials used. Prior teachings have suggested that Velcro connectors on compression devices should be small enough to allow for release in the event of over-pressurizing an inflatable compression device; however, Applicant gives limited credence to such teachings and has found that larger tabs may be desired in order to ensure secure enclosure of the foot in normal operation. Size increases of tabs 8 and 88, though, should be balanced against desire not to have Velcro hook connectors overlapping to a degree that would engage the skin of foot 100. Specifically, Applicant, in alternative embodiments (not shown), has utilized larger Velcro hook connectors at the location of Velcro hook connector 88 in FIG. 2, and has found that the width of tab 5 can be increased to accommodate such larger Velcro connectors.

As is evident in FIG. 2, the orientation of tab 5 is substantially perpendicular to the orientation of tab 7. Similarly, tabs 4 and 6 extend in directions generally perpendicular to one another, although tabs 4 and 6 are more rounded at their distal ends 4" and 6" than are tabs 5 and 7. The distal ends 4" and 6" of tabs 4 and 6 are inflatable in the preferred embodiments; whereas the distal ends 5" and 7" of tabs 5 and 7 are not inflatable and are provided with Velcro connectors 8 and 88 stitched thereto, respectively. Distal ends 5" and 8" are also considered squared relative to the more rounded ends 4" and 6". In use, the uppermost edge of wrap 1A is provided by edge 5' which spans between tabs 5 and 7. Unlike each of the other edges, 5', 6' and 8' that span between tabs 4–7, edge 4' (spanning between the distal ends 4" and 6") has a convex shape, although only slightly so. The inflatable ends 4" and 6" of tabs 4 and 6 are also convex, although more so than edge 4'.

A blank (i.e., non-inflatable) central portion 5''' is provided at the proximal end of tab 5, in the part of wrap 1A spanning between weld 10 and connector 88. The purpose of blank central portion 5''' for tab 5 is to ensure that connector 88 adequately overlaps tab 4 on varying sizes of feet (thereby ensuring against contact between the Velcro hooks of connector 88 and the skin of foot 100), while also limiting the size of bladder 9 by not extending it over blank central portion 5'''. The balance was drawn principally because the tab 5 is sized such that blank central portion 5''' will overlap tab 4 (which is already inflatable) in most applications. The position of inflatable extension 7 is oriented relative to the rest of wrap 9 to wrap around more of the vein-containing portions of a patient's lower leg, as opposed to right around the back of the heel 102 and ankle 104 of leg 105.

Referring especially to FIGS. 1, 6 & 7, fitting 11 is a tubular fluid connector having an elbow form to reduce the extent of protrusion from sheet 2. Its elbow shape also enables connection of a fluid hose 30A (shown in FIG. 1) to the fitting 11 and helps minimize the possibility of kinking hose 30A during use. A conventional, barbed hose connector 18 is incorporated in the outermost end of fitting 11 to enable connection with hose 30A, although a properly sized hose 30A could also be connected merely by a friction fit with fitting 11. Fitting 11 is formed of a compatible heat-weldable material and has a base flange 12. This fitting is inserted from the inside of sheet 2 through a hole 12' punched in fabric sheet 2 and is then positioned so that flange 12 contacts the heat-weldable inner surface of fabric sheet 2. The engagement between flange 12 and sheet 2 is then welded fluid-tight to completely seal the bladder 9A from leakage.

As suggested above, tabs (or "extensions") 4–7 extend generally away from each other. With wrap 1A laid flat, tabs 5 and 4 lie on opposite sides of wrap 1A, extending generally along the line. "7A—7A" in FIG. 3. Extension or tab 7 of foot wrap 1A lies substantially perpendicular to line "7A—7A" and is considerably longer than tab 5. In other embodiments (not shown), tab 7 is less perpendicular than pictured in FIGS. 2–7. Hook connector patches 8 and 88 are sewn or welded at or near the distal ends of 5" and 8" tabs 5 and 7, respectively, on the outer surface of inner sheet 3.

As shown best in FIGS. 2 and 3, the convoluted J-shape of bladder 9 includes circular recesses 53–56 in the midst of bladder 9. Such recesses 53–56 combine with other features of bladder 9 to optimize compression of foot 100. Particularly, recesses 53–56 are oriented to minimize excessive billowing of bladder 9, particularly over the less compressible areas of each lateral side of foot 100. Inflatable tabs 4 and 6 remain inflatable despite recesses 53–56 to provide compression of other regions of the foot. The preferred positions and orientations of recesses 53–56 are best evident in the FIGS. 2 and 3 of the drawings.

In part by weld 10 and elsewhere by welds 10, the outer perimeter 14 of the entire foot wrap 1A is RF-welded to join sheets 2 and 3, thereby forming a composite fabric wrap 1A with the single tubular fitting 11 mounted therein. Such simplicity is in striking contrast to the large and complex foot wraps heretofore employed for similar purposes. This preferred embodiment weighs less than 6 ounces and is approximately 38 centimeters in the direction of line "7A—7A" of FIG. 2 by 39½ centimeters in the perpendicular direction of line "7B—7B". Other forms of connecting the sheets may be used, such as by stitching, although commensurate sacrifices of inventive aspects will probably be associated with such a change.

Figure 8A:
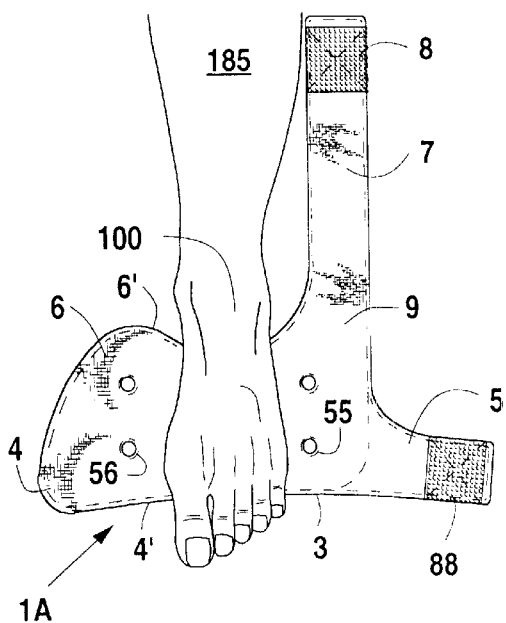
FIGS. 8A–8D illustrate the manner of operatively applying a foot wrap 1A to a foot 100.
Figure 8B:
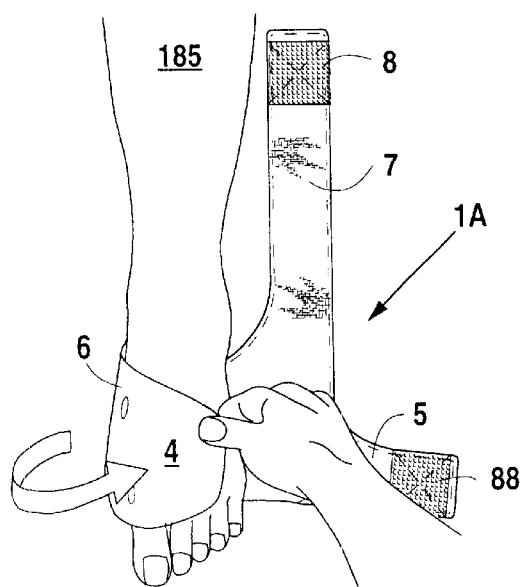
Figure 8C:
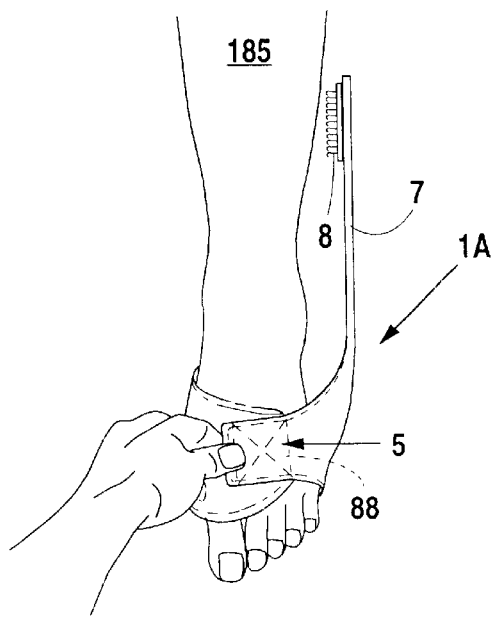
Figure 8D:
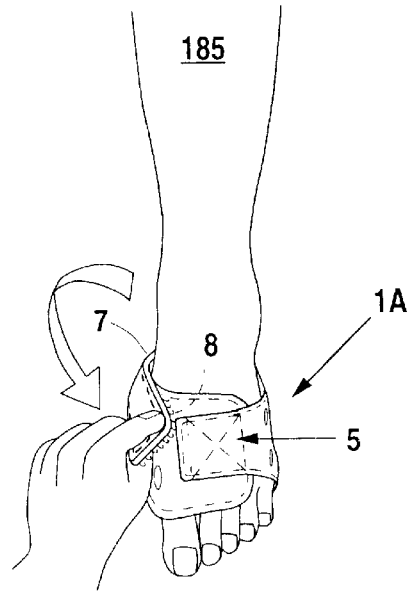

Referring to FIGS. 8A–8D, foot wrap 1A also stands out for its ease and simplicity of use. First place the foot wrap in the flat position shown in FIG. 8A and place the foot 100 over the central portion of bladder 9. Foot 100 should be positioned on bladder 9 in a way such that the center of heel 102 of foot 100 is positioned just off of bladder 9 and inside the arc of heel edge 6'. The length of foot 100 should extend across bladder 9 in a direction parallel to the length of tab 7, in a path directly between circular welds 55 and 56, such that the foot lies in contact with inner sheet 3 of wrap 1A. Then, as in FIG. 8B, wrap tab 4 and 6 around the foot 100, with tab 6 naturally following and extending toward the back of the leg 105. Tab 4 should wrap over the top of the foot 100. Then wrap tab 5 over tab 4 as in FIG. 8C, so tabs 4 and 5 overlap on the top of the foot. Adjust the tightness of the fit to the degree desired (preferably snug) and press the hook patch 88 of tab 5 onto the outer surface of tab 4 so they form a secure connection. Then, to completely secure the bladder 9 to the foot 100, draw tab 7 around the back of the foot 100 as shown in FIG. 8D and pull it snug. Hooked tip 8 (shown in FIG. 8A) is then pressed onto the outer surfaces of tab 6 where it overlaps on the side of the foot 100. The foot wrap 1A is now locked in position until the fastenings 8 and 88 are peeled open for removal of the foot wrap 1A. This procedure can be accomplished in a few seconds, and removal requires only pulling of the two tabs 5 and 7.

Minor adjustments in the preferred position of the bladder 9 relative to the foot 100, if required, may include loosening and repositioning one or both tabs 5 and 7 as necessary. The relative lengths of tabs 4, 5, 6 and 7 are not fixed but must meet the requirement of overlapping sufficiently to form a secure fastening when wrapped around foot 100. Thus tab 4 may be shorter than tab 5, although the general proportion illustrated in FIGS. 1–8 is preferred. The foot wrap 1A will fit a wide range of foot sizes without change in the application technique. If necessary, feet of very small persons may be fitted through the use of firm padding above the instep and behind the heel to simulate a larger foot while allowing the bladder to act against the sole of the foot through the padding.

The size and shape of the bladder 9 and foot wrap 1A in relation to foot 100 may also be larger than shown, even enclosing the entire foot, while still appreciating many aspects of the invention. Although not included in the pictured embodiments in view of the objects of reducing complexity, size, weight and material cost, among others it is preferred to provide a bladder which fully encloses the foot or, perhaps more practically, extends to just enclose the toes of the feet. However, larger capacity pumps and/or slower cycle times must be employed with such alternative embodiments in order to compensate for the bladders having larger volumes.

Nonetheless, without encompassing the entire foot, air and foot moisture vapor can exchange between the foot and the foot wrap from both the front and rear areas where the foot wrap 1A wraps onto the foot 100. Circular recesses 53–56 are also provided with holes 53'–56' in the central portions thereof to provide for greater ventilation for the foot 100. Such holes 53'–56' may be punched, cut or die-cut central to circular welds 53–56 in the same or similar manner to the formation of the outer perimeter 10' of foot wrap 1A.

During the deflated phase of pumping, the fit is looser and air can more easily diffuse the covered areas of skin beneath the foot wrap 1A. With proper materials as in the preferred embodiment, such diffusion is not as critical though, because the material of sheet 3 is vapor permeable—allowing moisture to vacate the skin surface through sheet 3. The soft inner surface of foot wrap 1A, which is also the outer surface of sheet 3, may be covered with a springy, open pile or other lining which promotes the entrance of air into the area between sheet 3 and the foot 100 during the decompression phase. An alternative embodiment of the invention may use a non-vapor permeable sheet 3 having an outer surface with such air movement promoting characteristics.

This small, lightweight, inexpensive foot wrap 1A in itself is sure to fill an important need in modern medicine. Nonetheless, as will be evident from this description to those of ordinary skill in the art, many aspects of this invention may be appreciated with other compression devices, possibly in combination with other intermittent or sequential compression features or devices, and possibly employed on other parts of the body including the hand, the leg, the arm or combinations thereof—naturally, with commensurate sacrifices of certain aspects of this present invention.

Referring again to FIG. 1, the housing 20 of unit 501 will be discussed briefly. Housing 20 is an injection molded plastic housing that comprises front housing plate 27 and back housing plate 26 fastened together using any conventional means such as screws. Front housing plate 27 and back housing plate 26, once connected, form handle 23 which facilitates carrying of pump unit 501. The preferred embodiment's pump unit 501 as a whole weighs roughly ten pounds, although the shape of housing 20 is ideal for units of any weight that can be safely hand-carried and supported on the foot board or headboard of a patient-supporting bed. The components inside the pump unit 501 are preferably arranged so the center of gravity for the pump unit 501 is roughly concentric with the volumetric centroid of the housing 20, although great care need not be taken in this as long as the center of gravity is appreciably below the height where the hooks 21 rest on the foot board 600. Such a location is preferred in order to distribute the weight of unit 501 between its two mounting hooks 21A and 21B and to ensure the unit is not top-heavy, both for ease in carrying and stability in mounting. The shape of housing 20 and the relative positioning of hooks 21A and 21B naturally help ensure that the center of gravity is centrally located.

Figure 9:
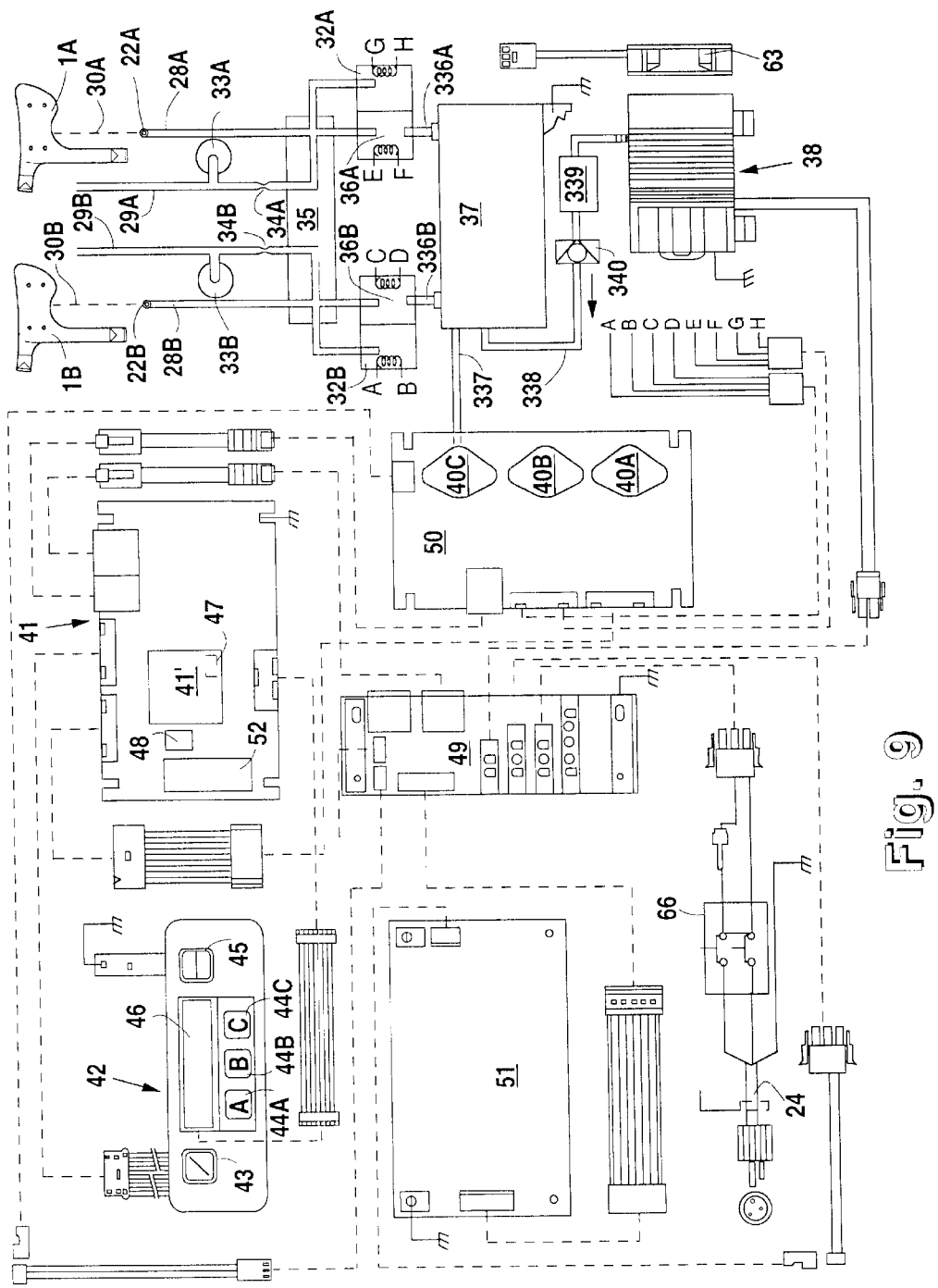
FIG. 9 shows a schematic layout of the electrical and pneumatic systems of the preferred embodiment shown in FIG. 1.

Referring still to FIG. 1 and also to FIG. 9, where more detailed features of system 500 are shown schematically, power switch 66 turns the pump unit 501 (and thus the system 500 as a whole) on and off. Power cord 24 is a conventional power cord for providing standard 115/120 volt, 60 Hz power to the pump unit 501. Preferably cord 24 is a hospital grade cord.

The links between pump unit 501 and foot wraps 1A and 1B are principally pneumatic. Right and left hose connectors 22A and 22B are the female members of conventional quick-disconnect air line connectors. Connectors 22A & 22B are firmly secured to front plate 27 of housing 20 to provide a connection inlet from foot pump housing 20 to the respective air hoses 30A and 30B of right and left foot wraps 1A and 1B. The ends of hoses 30A and 30B that connect to housing 20 are adapted with integral male connectors 31A & 31B for easy mating with connectors 22A & 22B. Connection and disconnection of connectors 31A and 31B can be done easily with one hand and little effort. The connections between hoses 30A & 30B and inlets 11A & 11B are completed with conventional barbed line connectors 18A and 18B. Connectors 18A and 18B provide relatively permanent, sealed connections for keeping the hoses 30 and wraps 1A & 1B integral.

Operator console 42 provides a user interface to the microprocessor of unit 501, allowing the user to either enter individual settings from a selection menu (discussed further herein) or select default settings. Operator console 42 basically comprises an LCD (liquid crystal display) assembly 46 formed in a membrane panel. LCD assembly 46 comprises a two-line, twenty character alphanumeric liquid crystal display which displays programming instructions, status updates, and alarm messages to the operator. The membrane panel of console 42 has integral switches 43–45 therein, namely: "PULSE ON/OFF" switch 43; operator selection switches 44A, 44B, 44C respectively designated "A", "B" and "C"; and "OPTIONS" switch 45. As will be evident to those of ordinary skill in the art, other switch configurations and/or options may be substituted within the scope of this invention. For instance, in one alternative embodiment the "PULSE ON/OFF" feature has been eliminated and switch 43 has been dedicated to silence any alarms, with appropriate labeling of switch 43. To eliminate that feature, the system 500 will always be in the air pulse therapy mode (see below) when the system is empowered, i.e. when main power switch 66 is ON.

The operation of system 500 is primarily controlled by the primary processor of pump unit 501, which is microcontroller 41. Micro-controller 41 is a conventional type of control board. As will be evident to those of ordinary skill in the art, the specific characters of micro-controller 41 are dictated by its intended operation, as described and evident further herein and in said Co-Pending U.S. Application (and other references included therein).

PULSE ON/OFF switch 43 both selects and de-selects an air pulse therapy mode for the system 500. If PULSE ON/OFF switch 43 is depressed to its ON state when the main power switch 66 is Off, the system 500 remains inoperative, but if PULSE ON/OFF switch 43 is depressed ON when the main power switch is ON, the controller of system 500 causes delivery of pneumatic pulses to the foot wraps 1A and 1B according to the currently set operating parameters. When system 500 is turned on, such parameters are preset to default to the last entered parameters, but they can be adjusted at any time thereafter by appropriate selection of the OPTIONS switch 45 and operator selection switches 44A–C when the main power switch 66 is ON, regardless whether switch 43 is actuated. Turning the PULSE ON/OFF switch 43 OFF during operation will turn off compression/decompression cycling.

The remaining basic components of pump unit 501 are shown schematically in FIG. 9, including without limitation GPDU Power Distribution Board 49, power supply board 51, and air control board 50. On the pneumatic side, the unit 501 basically includes: compressor 38, compressor cooling fan 36, accumulator 37, two normally-closed inflation solenoid valves 36A & 36B, two normally-opened deflation solenoid valves 32A & 32B, manifold 35, air hoses therebetween, and various other lesser components which will be clear from the drawings, particularly in view of the following more detailed descriptions of the operation of system 500.

The operating protocol of operator console 42 will now be described. When the main power switch 66 for the system 500 is first turned ON, the microcontroller 41 (FIG. 9) displays a query on the top line of LCD assembly 46 requesting the operator to indicate whether there is a new patient. The bottom line of LCD assembly 46. displays the choices "YES" or "NO" above operator selection switches 44A or 44B, respectively. Upon selection of "YES" by depressing switch 44A, the operator has 5 seconds to depress OPTIONS switch 45 (discussed herein). Otherwise, micro-controller 41 automatically stores the default values for the pump's settings (discussed herein) from ROM 52 into RAM 47 (see FIG. 9). A selection of "NO" or no selection within 30 seconds causes micro-controller 41 to retrieve from the power down memory (discussed herein) the settings stored in memory when the unit was last powered off.

A depression of "YES" followed by a depression of OPTIONS switch 45 displays for user selection the first configuration (or "menu") option (see Table 1) on the top line of LCD assembly 46. Each subsequent depression of OPTIONS switch 45 sequentially displays a different configuration option for selection by the user (see Table 1). The bottom line of LCD assembly 46 simultaneously displays a selection of up to three choices for the configuration option displayed in the line immediately above. Those choices are displayed spaced across the second line of LCD assembly 46 with each choice centered above a corresponding operator selection "programming" switch 44A–44C. The operator enters a choice by depressing the operator selection switch 44A, 44B, or 44C that is directly beneath the appropriate display corresponding to the desired selection. Depression of operator selection switches 44A–44C appropriately signals micro-controller 41 to select the specified choice or query the operator for additional information. Therefore, by progressing through the display "option" menus and selecting the desired option parameters, the system operator may program all the options required for use during the operating session. However, if default values are selected, (note that values are always stored in power down memory) the default settings preferably are: both feet selected, cycle time 15 seconds, hold time 2 seconds, and left and right pressure levels of 150 mm Hg. Other default combinations, such as 150 mm Hg on both feet for a 3-second hold, with a 20-second cycle time have also been used with favorable results.

Table 1 discloses the menu selection options and the parameters available for use in the preferred embodiment of the present invention. Whenever the option selection process is complete, and whenever the "HOME" option is selected, the LCD display returns to one of three HOME displays as appropriate. The three HOME displays on the first line are: "Left and Right Pulse ON", "Left Only-Pulse ON", and "Right Only-Pulse ON". The second line of each HOME display has only one option—"(OFF)" positioned above switch 44C. Selection of "(OFF)" deactivates the foot compression features of system 500 and the "ON" and "(OFF)" LCD displays are changed to "OFF" and "(ON)", respectively.

TABLE 1

MENU SELECTION OPTIONS IN THE ORDER DISPLAYED

| Option | Description |
| --- | --- |
| Foot Pulse Select | Displays and allows the operator to select either one or both feet for pulse therapy. |

TABLE 1-continued

MENU SELECTION OPTIONS IN THE ORDER DISPLAYED

| Option | Description |
| --- | --- |
| Cycle Time Adjust? | "DECR INCR HOME" allows the operator to select the foot pump's cycle time; when both feet are selected, cycle time is total time required for foot wraps 1A and 1B (see FIG. 9) to sequentially inflate, hold, and deflate; cycle times range from 10 to 60 seconds, user selectable in 10 second intervals. |
| Hold Time Adjust? | "DECR INCR HOME" permits the operator to adjust the amount of time that the pressure is maintained in the respective foot wrap after inflation occurs; selections are 1, 2, 3, 4, and 5 seconds. |
| Left Foot Pressure Adjust? | "DECR INCR HOME" permits the user to adjust the foot pressure level in the left foot wrap from levels 2 through 10. |
| Right Foot Pressure Adjust? | "DECR INCR HOME" permits the user to adjust the pressure level in the right foot wrap from levels 2 through 10. |
| View Timers? | "LEFT RIGHT HOME" allows the operator to view the foot pump's total therapy and operating times (Note that left and right foot therapy times are individually displayed). |
| For Service Use Only | used by maintenance personnel to calibrate the foot pump. |

The pressure levels corresponding to the range of levels 2 to 10 in the first embodiment are roughly 25–200 mm Hg, although changes may be implemented within the scope of this invention. For instance, one alternative would be to change the selectable range to 1–5, corresponding to actual pressures from 120 to 190 mm Hg. For the purposes of disclosure, the timing and pressure setting ranges along with the system default settings of the preferred embodiment of the present invention have been described. The variability of such settings is highly beneficial. However, one of ordinary skill in the art will readily recognize that other ranges and default settings could be substituted.

Figure 20:
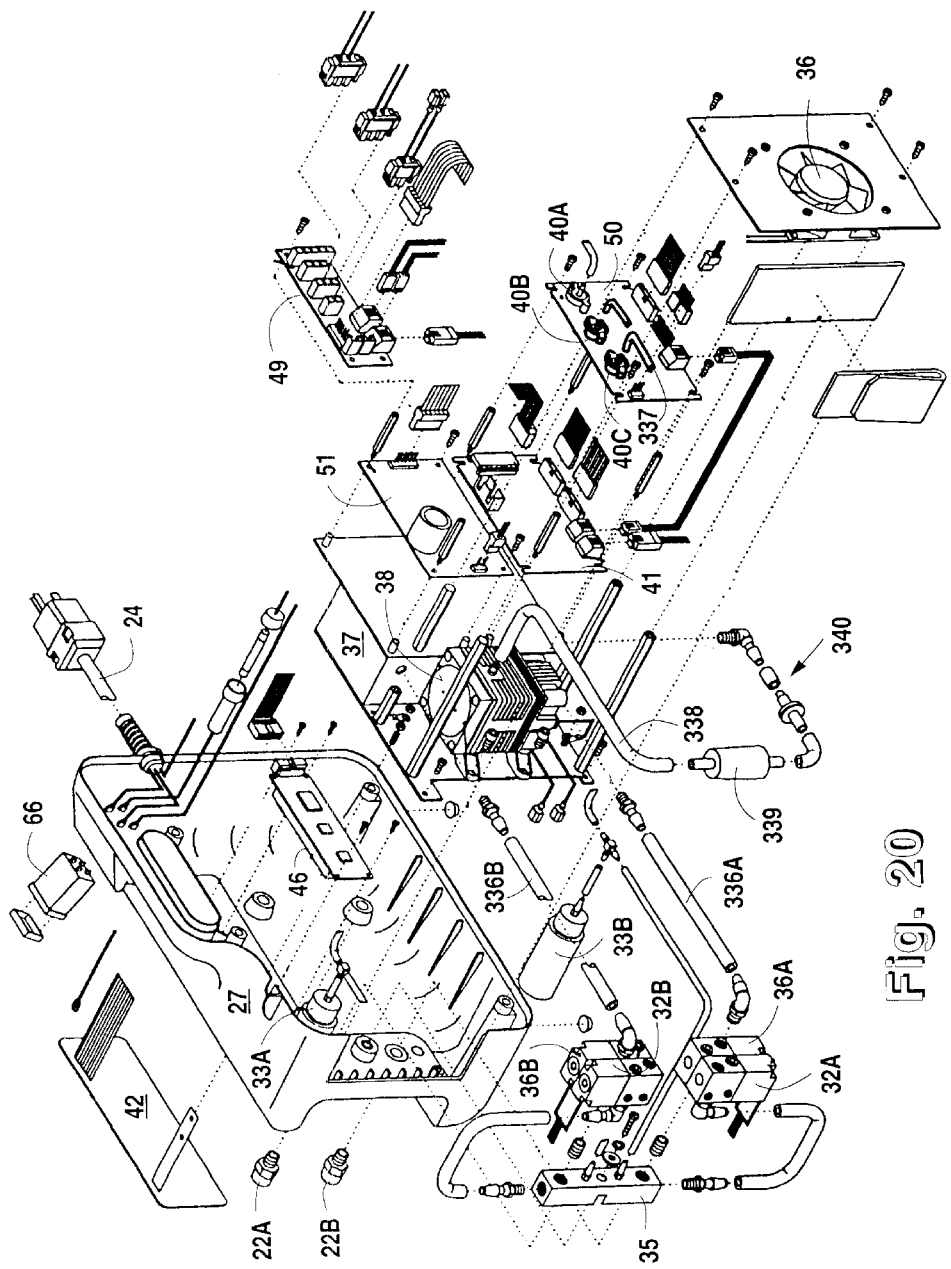
FIG. 20 shows an exploded view of the front portion of pump 20, illustrating many of the particular embodiments and relative configurations of the components schematically shown in FIG. 9.

Referring to both FIGS. 9 and 20, the preferred system component configuration and operation will be discussed in more detail. Foot wraps 1A and 1B, designed to be securely fastened to a human foot, are constructed from two sheets of fabric sewn or welded together to form an inflatable bladder 9 (described above). Alternative compression devices which are known in the art (such as compression sleeves or gloves) also could be used to appreciate many aspects of the invention.

Power cord 24 delivers the overall system power supplied from the standard 115V/120V, 60 Hz source to GPDU power distribution board 49 and, in turn, to Power supply board 51. Power supply 51 converts the standard 115V/120V AC to 12V DC and supplies the 12V DC back to power distribution board 49. Power distribution board 49 distributes the 115V/120V AC and the 12V DC to each component according to the electrical lines pictured in FIG. 9 and according to each particular component's power requirements.

Compressor 38 provides the compressed air which is necessary to inflate the inflatable bladders 9A and 9B formed in foot wraps 1A and 1B. Accumulator 37 stores the compressed air generated by compressor 38 before delivery to foot wraps 1A and 1B. Micro-controller 41 polls PULSE ON/OFF switch 43 to determine when compressor 38 should be turned on or off. In the presently preferred embodiment, the compressor is always running. When the pressure in accumulator 37 reaches its maximum, compressor 38 simply turns the air without being capable of pumping it. Nonetheless, the system 500 could be modified such that the pressure requirements of the system factor in determining the operation of solenoid valves 32 and 36. Compressor 38 is turned on and off with the system 500 as a whole by actuation of switch 66. Fan 36 also operates to continually supply a flow of air over compressor 38 to prevent it from overheating.

In operation of the preferred embodiment, the operator may select either the right foot, left foot, or both feet for foot pulse therapy. As described before, such a selection is enabled by micro-controller 41 and console 46. If both feet are selected for therapy, foot wraps 1A and 1B alternately inflate and deflate to provide pressure against a patient's foot. However, for the purposes of disclosure, only operation of the right foot wrap will be described. However, it is to be understood that the left foot wrap operates in the same manner. In this description, the numeral designations "A" are sometimes left off the reference numerals in order to enable easier reading on either the left or right foot wrap systems. Right solenoid valve 36A opens to inflate right foot wrap 1A by allowing air pressure from accumulator 37 to be directed into manifold 35. Manifold 35 simultaneously directs that air pressure to each of: (a) right foot wrap 1A via hose 28A, quick connect 22A, and external hose 30A (shown best in FIG. 1); (b) right vent solenoid valve 32A; and (c) right foot wrap pressure sensor 40A via sensor hose 29A, which has restrictor 34A and expansion tank 33A along its course (the connection between pressure sensor hose 29A is not shown in FIG. 9 for purposes of clarity; for the same reason, the connection between pressure sensor 40B and sensor hose 29B is not shown). While foot wrap 1A is being inflated (and thereafter through the hold time) to the selected or default pressure, right solenoid valve 36A is held closed, thereby maintaining the air pressure in foot wrap 1A. After the operator-selected or default hold time elapses, right vent solenoid valve 32A opens, discharging the air from foot wrap 1A. The above cycle then repeats after the cycle time (i.e. the time between inflation) elapses.

The controller divides solenoid operation into four modes, as shown below:

|  | Pre-inflate | Inflate | Hold | Deflate |
| --- | --- | --- | --- | --- |
| INFLATE | OFF | ON | OFF | OFF |
| DEFLATE | ON | ON | ON | OFF |

An initial surge of compressed air occurs when right solenoid valve 36A is first opened. If right foot wrap pressure sensor 40A measures the initial surge of air, an erroneous pressure measurement would occur. That is, right pressure sensor 40A would measure the pressure level as being much higher than it actually is in bladder 9A. To prevent right pressure sensor 40A from measuring such an initial pressure surge, the air flow path to right pressure sensor 40A contains right restrictor 34A and right expansion tank 33A. Right restrictor 34A restricts the flow of compressed air into right expansion tank 33A, thus decreasing the flow rate of the compressed air. Right expansion tank 33A provides an increased volume for expansion of the compressed air. As the initial air surge expands into right expansion tank 33A, the air pressure decreases. Therefore, when right foot wrap pressure sensor 40A measures the initial surge of air pressure, that measurement approximates the actual pressure being delivered from compressor 38 via accumulator 37 rather than the initial surge. Hence, the combination of restrictor 34A and tank 33A (and to an extent, each of them individually) serve as means for eliminating spikes in the pressure feedback sensed by sensor 40A.

Right foot wrap pressure sensor 40A, a conventional pressure transducer in the preferred embodiment, converts the pressure delivered to right foot wrap 1A from accumulator 37 into an electrical signal representative of that pressure. An amplifier and an analog-to-digital (A/D) converter (not shown) on air control board 50 convert that electrical signal to a digital signal readable by micro-controller 41. Micro-controller 41 then processes that pressure signal and sends solenoid control information to solenoid drive circuits (located on control board 41). Those drive circuits then control right solenoid inflate valve 36A and right vent solenoid valve 32A. Control of the solenoid inflate valve 36 and vent solenoid valve 32 by micro-controller 41' will be discussed herein with reference to the flow charts shown in FIGS. 10–12.

Pressure transducer 40C is identical to transducers 40A and 40B but is provided to sense the pressure in accumulator tank 37—not foot wraps 1A or 1B. Specifically, the air port of sensor 40C is in direct fluid communication with tank 37 through sealed line 337. The ultimate function of sensor 40C is to sense the drop in pressure after each opening operation of valves 36A or 36B, thereby giving controller 41' an indication of whether air is flowing freely out of tank 37. Micro-controller 41' uses that pressure reading for diagnostic display and audible alarm purposes. Micro-controller 41' determines if the pressure is too low, based on a digital signal from the A/D converter associated with the appropriate pressure transducer 40. Micro-controller 41', in combination with the pressure transducer 40C, thus, serves as a means for detecting errors in the operation of system 500 in its preferred embodiment—specifically errors due to obstruction in air flow to (and thus from, as well) the foot wraps 1A and 1B. If either line 28A or 28B are kinked, the pressure in tank 37 will not drop after opening the respective valve 36A or 36B. If controller 41' determines the pressure drop sensed by sensor 40C does not exceed a threshold level corresponding to roughly 5 mm Hg for five consecutive cycles, the controller 41' concludes there is a kink in line 28A or 28B and signals an audible alarm and visual alarm. In more detail, if the pressure drop after valve opening is too low, micro-controller 41' increments an error counter. Micro-controller 41' determines if the error counter is greater than or equal to a value of five. Then, if the error counter is greater than or equal to five, micro-controller 41' turns on an audible alarm, although the pump unit 501 continues to operate as before. As will be apparent to those of skill in the art, A/D converters (not shown) are associated with each sensor 40A–40C to enable interface with controller 41'.

Figure 10:
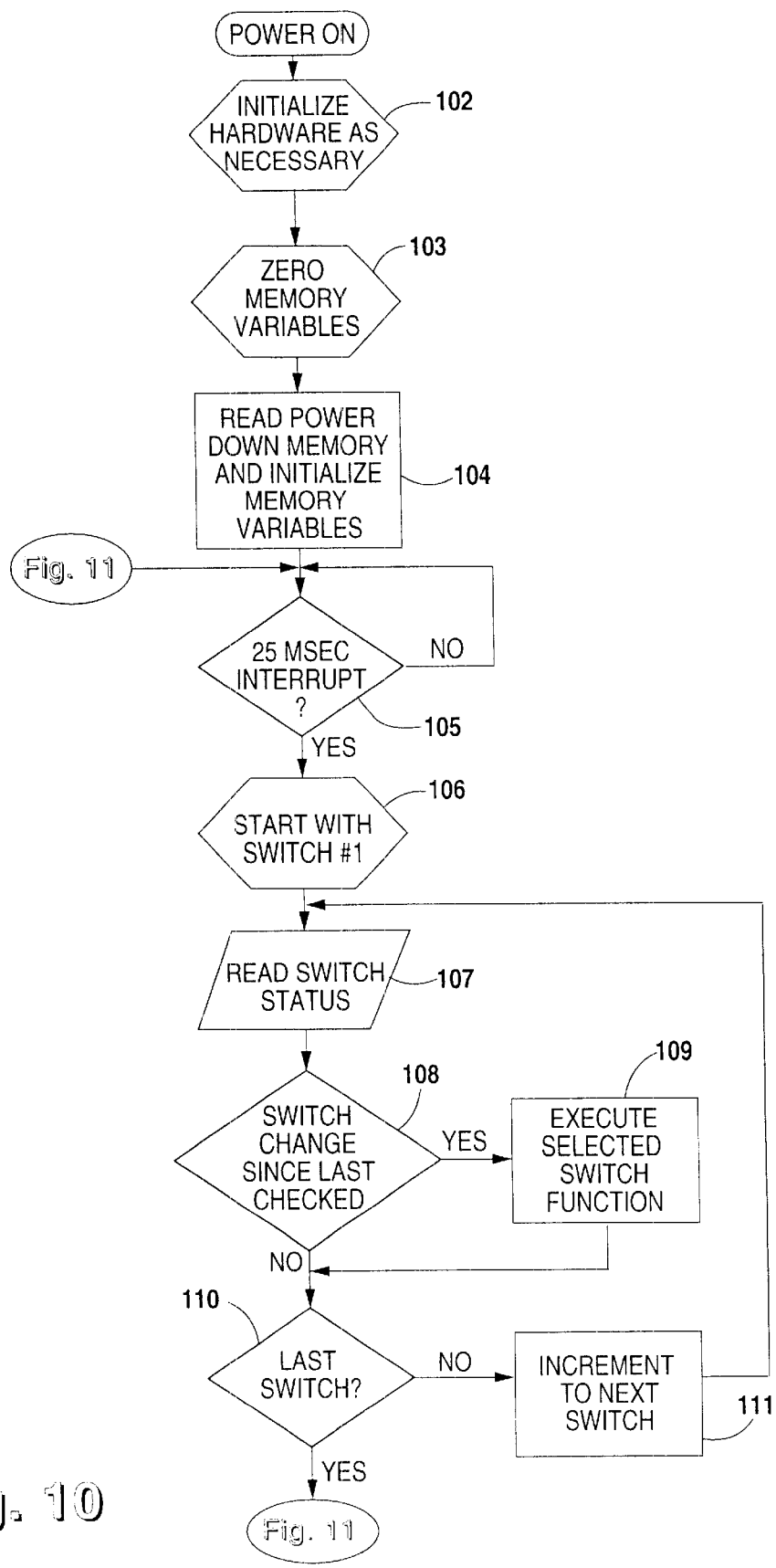
FIGS. 10–12 show flow charts which characterize the operation of the preferred embodiment shown in FIG. 1.
Figure 11:
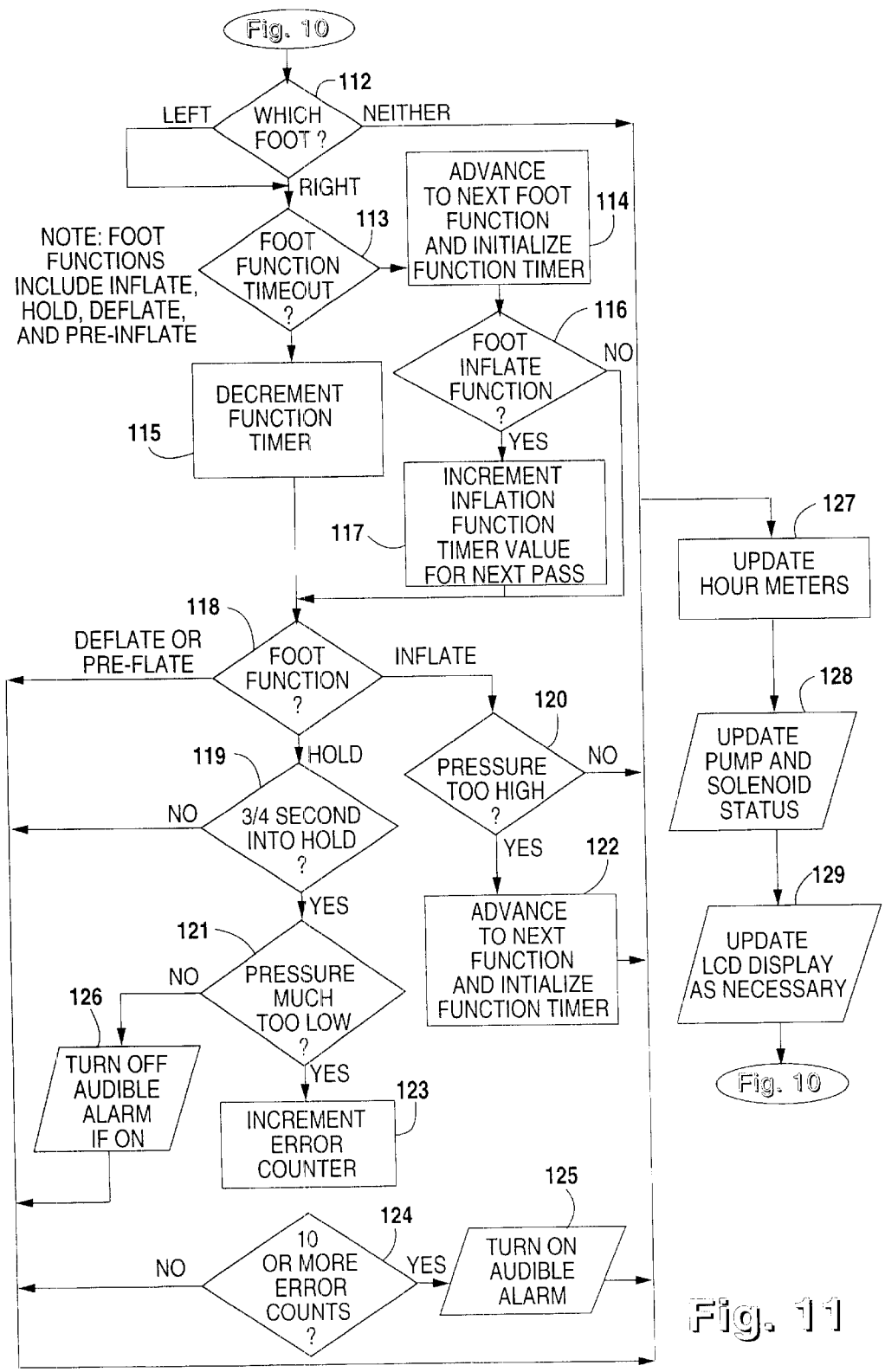
Figure 12:
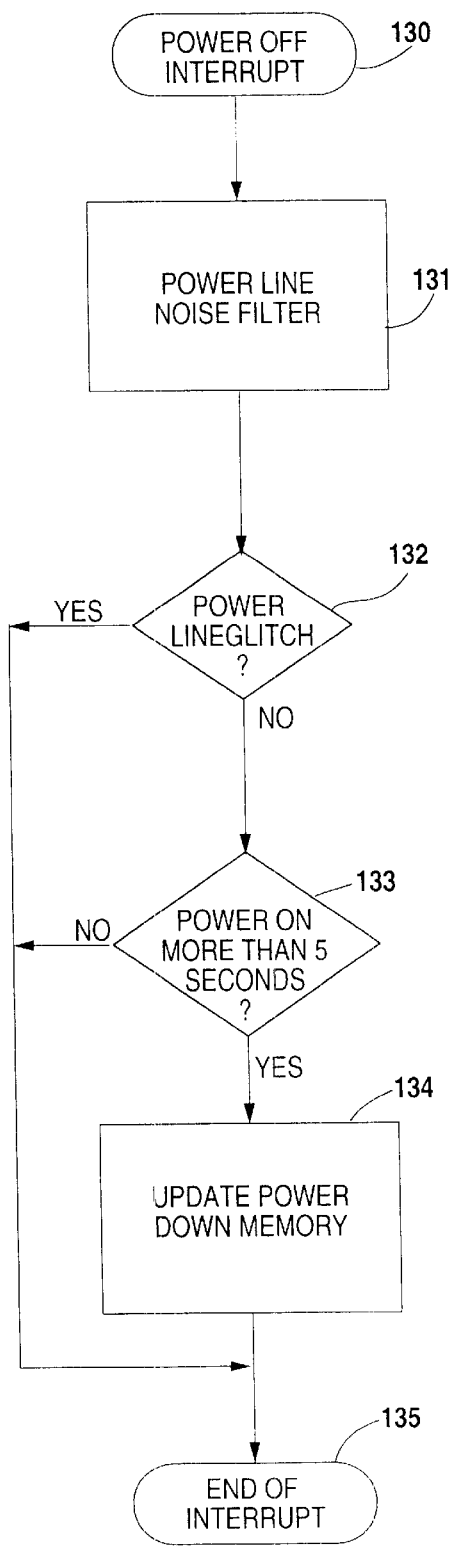
Figure 13:
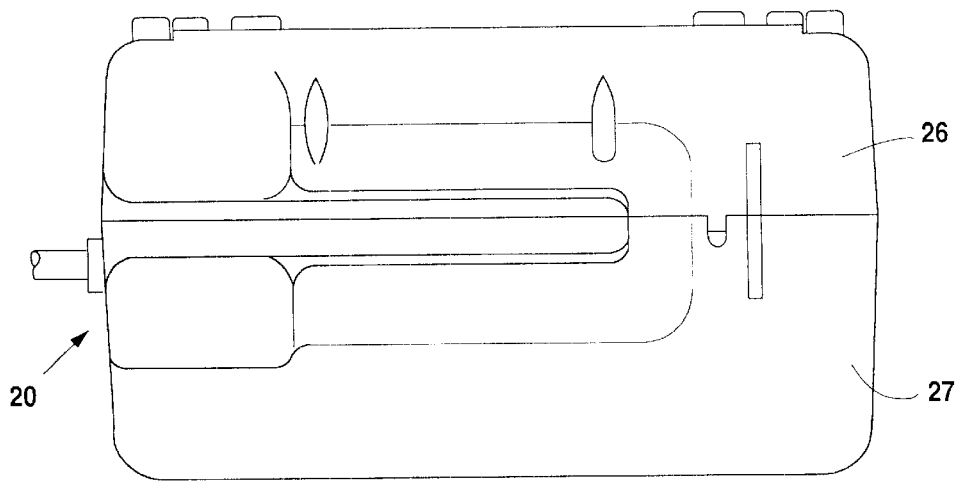
Figure 14:
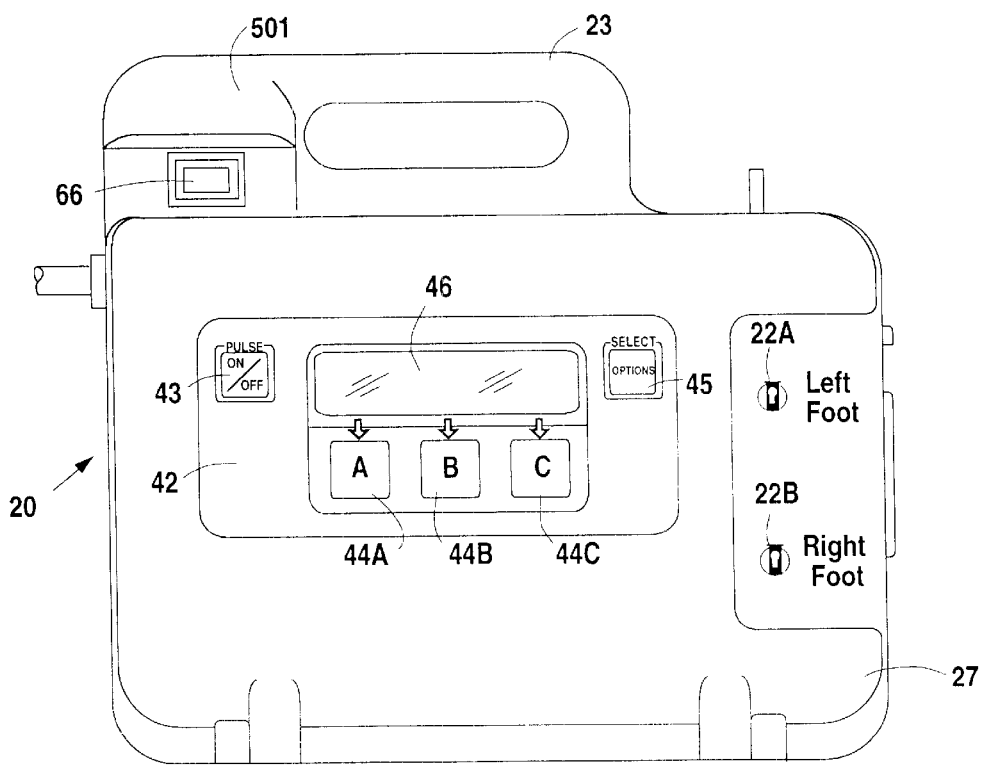
FIG. 14 shows a front elevation view of the pump housing 20, without certain details.
Figure 15:
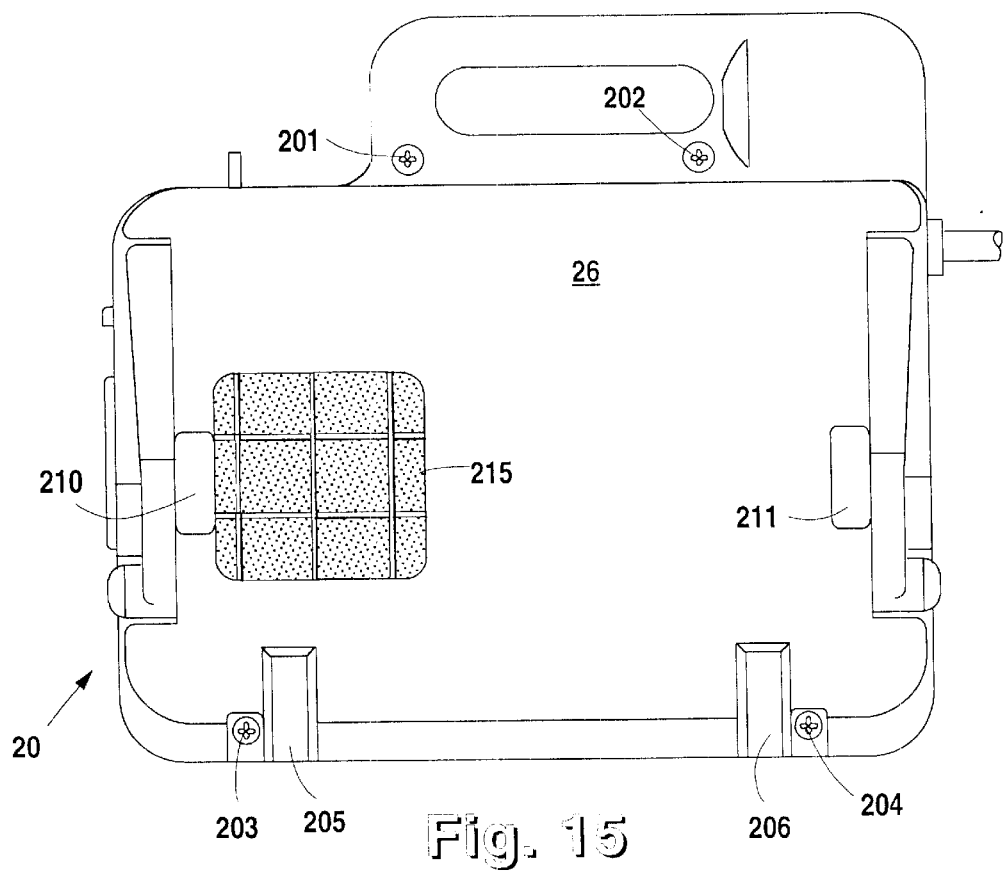
FIG. 15 shows a rear elevation view of the pump housing 20.
Figure 16:
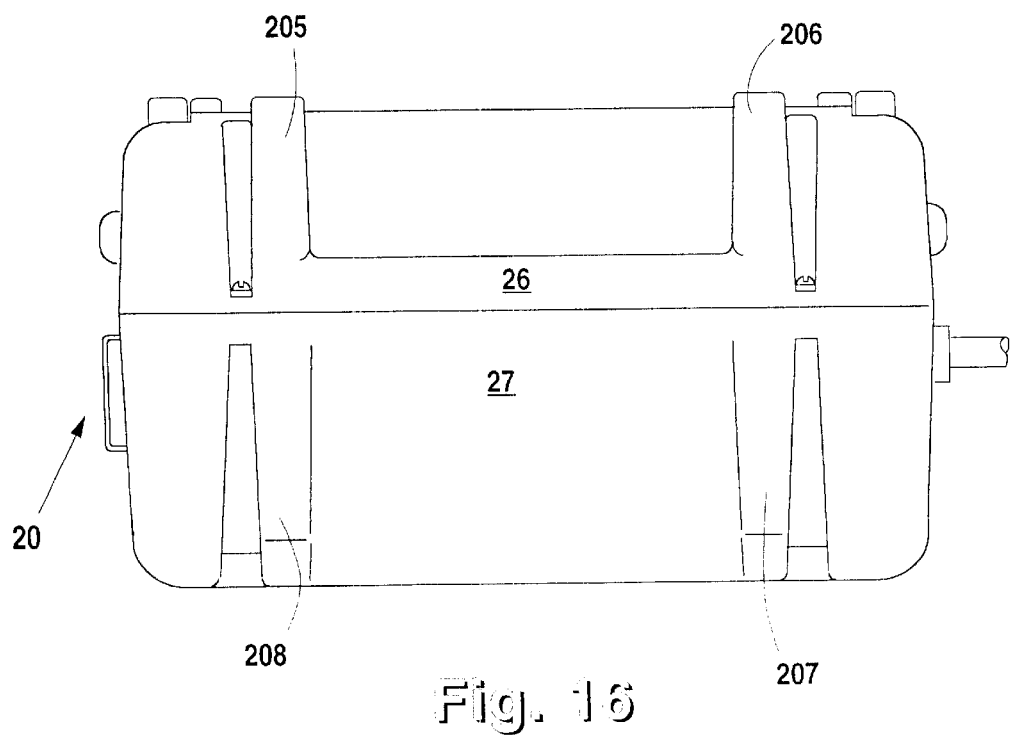
FIG. 16 shows a bottom view of the pump housing 20.

Referring to the flow chart shown in FIGS. 10–12, micro-controller 41' control of the preferred embodiment of the present invention will be described. Preferably, micro-controller 41' is a conventional micro-controller such as Signetic's 80C552 controller, which has one RAM chip 47 (along with other conventional components) integral therewith. After the power is turned on by depressing switch 66, micro-controller 41' actuates an initialization signal to its hardware components including the circuits controlling the compressor 38, the solenoids 32 and 36, and display 46. In step 103, micro-controller 41 places zeros in the variables contained in random access memory (RAM) 47. When the foot pump is powered down, its present configuration settings, referred to as power down settings, are stored in EPROM 48 and may be used as default settings for the next power up. Accordingly, in step 104, the power down settings stored in EEPROM 48 are read and stored in RAM 47.

Sequential polling of PULSE ON/OFF switch 43, operator selection switches 44A, 44B, and 44C, and OPTIONS switch 45 occurs every 25 milliseconds, as shown in steps 105–111. Step 106 informs micro-controller 41' to start its polling with switch 1. In step 107, micro-controller 41' stores the state of the polled switch in RAM 47 and in step 108 compares that state with its previous state. If the switch has changed states, micro-controller 41' advances to step 109 and executes the selected switch function and stores the operator setting or default setting retrieved from ROM 52 (actually a conventional EEPROM in the preferred embodiment) into RAM 47. Micro-controller 41' then advances to step 110. Alternatively, micro-controller 41' advances directly to step 110 if the switch did not change state. In step 110, micro-controller 41' determines if the last switch has been polled. If the last switch has not been polled, micro-controller 41' increments to the next switch in step 111 and returns to step 107 where it reads the state of that switch. Once all the switches have been polled, micro-controller 41' advances to step 112.

In step 112, micro-controller 41' reads the settings from a status register located in RAM 47 to determine which foot (if either) will be processed for the current cycle. If Pulse is switched OFF, micro-controller 41' advances to step 127 and updates the operating time meter, which records total operating time. In step 128, micro-controller 41' actuates signals to both power distribution board 49 and pressure control board 50 to control unit 501. More specifically, in response to the signals of step 128, power distribution board 49 turns compressor 38 on or off, and pressure control board 50 energizes or de-energizes (as necessary) the inflate solenoid valves 36A and 36B and/or the vent solenoid valves 32A and 32B. In step 129, micro-controller 41' refreshes the present display of LCD assembly 46 as necessary. After updating the display on LCD assembly 46, micro-controller 41' returns to step 105 to continue the present foot function mode. This loop is repeated every 25 milliseconds.

The four foot function modes will now be discussed. This path is followed anytime that PULSE is switched ON. Microcontroller 41' sequentially and repeatedly advances through the following foot function modes: deflate to pre-inflate, pre-inflate to inflate, inflate to hold, and hold back to deflate. The vent valve and the inflate valve in the preferred embodiment are identical body-ported three-way solenoid valves. The vent solenoid valve is fluidly connected to be normally opened, and the inflate solenoid valve is connected to be normally closed. In the deflate mode, the vent solenoid valve corresponding to the inflated foot wrap opens releasing any air pressure in the inflatable bladder. The pre-inflate mode causes the normally opened vent solenoid valve to close, while the inflate solenoid valve remains closed. Then during the inflate mode, the inflate solenoid valve corresponding to the foot wrap that is to be inflated is opened, allowing air pressure to fill the inflatable bladder while the vent solenoid is held closed. After each inflate mode, the opened inflate solenoid valve closes while the vent valve remains closed, thus maintaining the air pressure in the foot wrap during the hold mode.

The above cycle continuously repeats during foot pump operation. However, when the pump unit 501 is initially turned on, the beginning inflate modes operate under a ramping function. The ramping feature is beneficial because the pressure sensation delivered to a patient's foot during the first few inflate modes may startle the patient. Accordingly, the ramping feature reduces patient alarm by allowing the patient to gradually become acclimated to the pressure pulses delivered to the patient's foot. Upon system start-up, the initial pressure in the first inflate mode is low because the inflate solenoid valve is only briefly energized (25 milliseconds in the preferred embodiment). During each subsequent inflate mode, the inflate solenoid valve energization time increases by 25 milliseconds until that energization time reaches the operator selected or default pressure level, and the foot pump is delivering the desired pressure to the patient's foot. Other embodiments include ramping feature inflate times starting at 100 milliseconds and increasing by 50 millisecond increments.

Again referring to step 112, if the left or right foot is selected, micro-controller 41' advances to step 113 and reads the value of the foot function counter. The value stored in the foot function counter represents the time remaining for the foot function in progress. Foot functions include inflate, hold, deflate and pre-inflate. Each foot function counter value is determined on the basis that micro-controller 41' requires 25 milliseconds (in the preferred embodiment) to execute steps 105–129, thereby completing one processing loop, which includes a foot function counter decrement (step 115). For example, if the user selects a one second hold time, micro-controller 41' places a value of 40 in the foot function counter. Micro-controller 41' enters that value into the foot function counter at the beginning of a hold function because 40 loops through steps 105–129 equals one second (40 loops times 25 milliseconds equals 1000 milliseconds, or one second). Therefore, as micro-controller 41' decrements the hold mode foot function counter during each pass through step 115, the inflate solenoid valves and vent solenoid valves will remain closed for one second.

The hold, deflate, and pre-inflate modes have fixed foot function counter values corresponding to each operator or default time selection as calculated above. However, because of the pressure ramping feature, the inflate mode foot function counter begins at 1 (corresponding to a real time of 25 milliseconds) and is incremented by 1 during each subsequent inflate mode until the desired pressure is reached. Thus, the solenoid valves remain open an additional 25 milliseconds through each subsequent inflate cycle. Once the desired pressure is achieved, micro-controller 41' no longer increments the inflate mode foot function counter.

Although for the purposes of a preferred embodiment, micro-controller 41' requires 25 milliseconds to perform the functions disclosed in steps 105–129, one of ordinary skill in the art will readily recognize that any delay time could be properly substituted. Variations on the ramping feature could also be substituted. As an example that other embodiments are being adapted to include solenoid energizing time at 100 milliseconds is initiating inflation and incrementing it by steps of 50 milliseconds (as opposed to the 25/25 times described previously).

In step 113, if the foot function counter is not zero, micro-controller 41' advances to step 115 and decrements the foot function counter by 1. Micro-controller 41' then advances to step 118. If the foot function counter is zero, micro-controller 41' has completed a foot function inflate, hold, deflate or pre-inflate. Accordingly, micro-controller 41' advances to step 114 and increments to the next foot function and places the value corresponding to that foot function into the foot function counter. Next, in step 116, micro-controller 41' determines whether the present foot function is in the inflate mode. If the foot function is in the inflate mode, micro-controller 41' advances to step 117 and increases the previous foot function inflate count by 1 (corresponding to 25 milliseconds) for use during the next inflate cycle. However, if the inflate mode has reached the user selected or default pressure as determined in step 120 (discussed herein), micro-controller 41' will not increment the foot function counter. If the foot function is not in the inflate mode, micro-controller 41' advances directly to step 118.

In step 118, micro-controller 41' determines whether the foot function is in the deflate, pre-inflate, hold, or inflate mode. If in step 118, the foot function was in the inflate mode, micro-controller reads a pressure signal from the respecting pressure sensor and advances to step 120. In step 120, micro-controller 41' determines if the pressure in the foot wrap is too high. That is, micro-controller 41' determines if the foot wrap pressure has exceeded the operator selected or default pressure. If the measured pressure is below the operator selected or default pressure, micro-controller 41' advances to step 127 and updates the operating time meter. In step 128, if the solenoid valve corresponding to the foot wrap to be inflated is de-energized, micro-controller 41' energizes it via pressure control board 50. However, if the solenoid valve 36 is already energized, micro-controller 41' rewrites the energization signal to pressure control board 50. (Note that the vent solenoid status is updated as well.) Micro-controller 41' then updates LCD assembly 46 and returns to step 105 to continue the present foot function.

However, if, in step 120, micro-controller 41' determines that the actual pressure is above the desired pressure, it advances to step 122. In step 122, micro-controller 41' increments to the next foot function (hold in this case) and places the foot function counter value corresponding to that foot function in the foot function counter. Micro-controller 41' then updates the operating time meter in step 127. In step 128, micro-controller de-energizes, via pressure control board 50, the inflate solenoid valve that had been energized during the inflate mode. The vent solenoid status is updated as well. Next, micro-controller 41' updates LCD assembly 46 and returns to step 105 for execution of the next foot function mode.

Micro-controller 41' is provided with two methods in the inflate mode to stop compressed air delivery to the foot wraps. First, micro-controller 41' monitors the pressure developed in the foot wrap during inflation, and if that pressure exceeds the operator selected or default pressure value, micro-controller 41' immediately increments to the next foot function and closes the energized solenoid valve (steps 120, 122 and 128). Alternatively, if the air pressure ever exceeds the desired pressure, micro-controller 41' delivers compressed air for the incrementing interval defined in the foot function counter. That is, micro-controller 41' allows inflation of the foot wrap until the inflate mode foot function counter is decremented to zero. Once the foot function counter reaches zero, micro-controller 41' increments to the next foot function and de-energizes the energized solenoid valve, thereby stopping air pressure delivery to the foot wrap. Thus, micro-controller 41' stops compressed air delivery to the foot wrap when either the inflation pressure exceeds the user specified or default value, or the inflate mode foot function counter reaches zero, whichever occurs first. (As noted earlier in this document, the inflate time valve in the preferred embodiment is ramped up in 25 millisecond intervals.)

Again referring to step 118, if the foot function is in the hold mode, micro-controller 41' advances to step 119 and determines whether at least ¾ of a second of the hold time has elapsed. If at least ¾ of a second of the hold time has not elapsed, micro-controller 41' advances to step 127 and updates the operating time meter. In step 128, if the inflate mode foot function counter was completely decremented to zero, micro-controller 41' will de-energize via pressure control 50 the solenoid valve energized during the preceding inflate mode. However, if the inflate mode was ended because the air pressure in the foot wrap became too high, the energized solenoid will already have been de-energized, and micro-controller 41' will only rewrite the de-energization signal. Micro-controller 41' then updates the display on LCD assembly 46 in step 129 and advances to step 105 to continue the present foot function mode.

If the elapsed hold time is equal to ¾ of a second, micro-controller 41' reads the pressure value measured by the respective pressure sensor and advances to step 121. Step 119 provides a ¾ of a second delay before pressure measurement to permit the air pressure in the foot wrap to settle so that the pressure sensor makes an accurate pressure reading. Micro-controller 41' uses that pressure reading for diagnostic display and audible alarm purposes. In step 121, micro-controller 41' determines if the pressure is too low, based on a digital signal from the A/D converter associated with the appropriate pressure transducer 40. Micro-controller 41', in combination with the pressure transducer 40, thus, serves as a means for detecting errors in the operation of system 500 in its preferred embodiment. If the pressure is too low, micro-controller 41' advances to step 123 and increments an error counter. In step 124, micro-controller 41' determines if the error counter is greater than or equal to a value of 5. If the error counter is greater than or equals to 5, micro-controller 41' turns on an audible alarm in step 125 and advances to step 127. Although the audible alarm sounds, the pump unit 501 continues to operate, and no changes are made. In step 127, micro-controller 41' updates the operating time meter. In step 128, micro-controller 41' rewrites the present actuation signals to power distribution board 49 and pressure control board 50. In step 129, micro-controller 41' updates the display as necessary on LCD assembly 46 and returns to step 105 to continue the present foot function mode. However, if the error counter is below 5, micro-controller 41' advances directly to step 127 without turning on the audible alarm. In steps 127–129, micro-controller 41' updates the operating time meter, rewrites the actuation signals to power distribution board 49 and pressure control board 50, and updates the display as necessary on LCD assembly 46. Micro-controller 41' then advances to step 105 to continue the present foot function.

Again referring to step 121, if the measured pressure is not too low, micro-controller 41' advances to step 126, turns off the audible alarm (if it was on), and sets the error counter to zero. Micro-controller 41' then advances to steps 127. In steps 127–129, micro-controller 41' updates the operating time meter, rewrites the actuation signals to power distribution board 49 and pressure control board 50, and updates the display as necessary on LCD assembly 46. Micro-controller 41' then advances to step 105 to continue the present foot function.

Referring again to step 118, if the foot function is in the deflate or pre-inflate mode, micro-controller 41' advances directly to step 127 to update the operating time meter. In step 128, micro-controller 41' changes the actuation signal to pressure control board 50 to either energize or de-energize the vent and inflate solenoid valves dependent upon whether the foot function mode is deflate or pre-inflate. For example, if the foot function is in the deflate mode, the vent solenoid valve will open and the inflate solenoid valve will be closed to allow the deflation of the inflated foot wrap. However, if the foot function is in the pre-inflate mode, the vent solenoid valve will be closed in preparation for the next inflate foot function mode. Also in step 128, micro-controller 41', via power distribution board 49, stops, starts or continues the delivery of power to compressor 38. After micro-controller 41' updates LCD assembly 46 in step 129, it advances to step 105 where the loop is repeated every 25 milliseconds.

Figure 4:
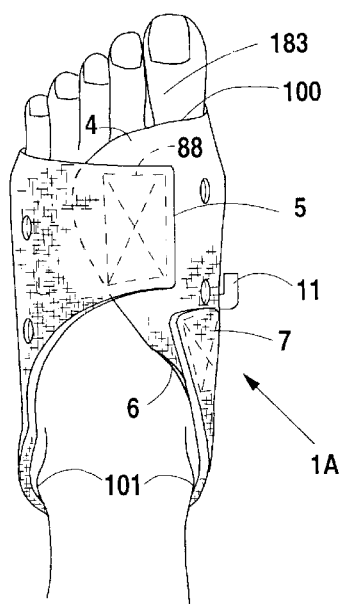
FIG. 4 shows a top view of the foot wrap 1A in place on a human foot.
Figure 5:
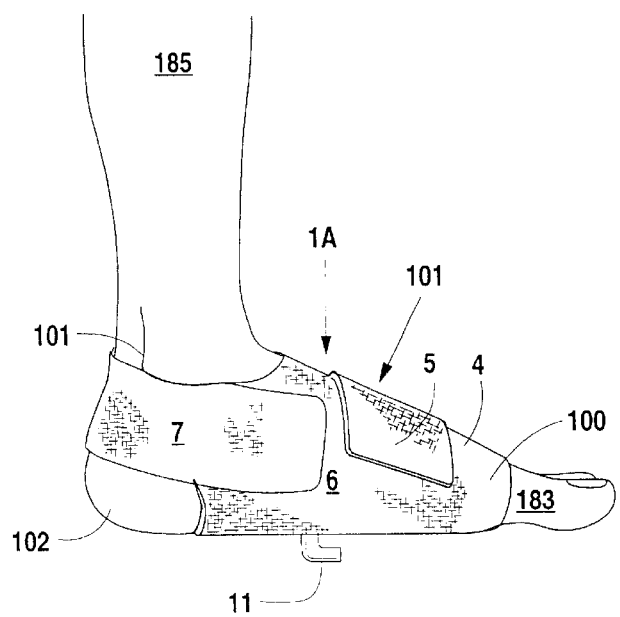
FIG. 5 shows a side view of the foot wrap 1A in place on a human foot.

Operation of the power down memory of the preferred embodiment of the present invention will be described in reference to the flowchart shown in FIG. 4. In step 130, if the power is turned off or there is a power line transient (e.g. a power surge or noise), micro-controller 41' executes the power off interrupt. In step 131, micro-controller 41' executes a software filter loop to reduce susceptibility to power line noise transients. In step 132, micro-controller 41' determines if the power has been turned off or if the power line merely experienced a transient. If the power line experienced a transient, the interrupt routine is exited and the pump unit 501 continues to operate normally. If micro-controller 41' determines that AC power has been turned off, microcontroller 41' advances to step 133 and determines if the power has been on for more then 3 seconds. If the power has been on for more than 3 seconds, micro-controller 41' advances to step 134 and writes date into EEPROM power down memory 48 values representing the last operator entered foot function settings. Micro-controller 41' then advances to step 135 and exits the power down routine. However, if the power has not been on more than 3 seconds, micro-controller 41' advances to step 135 and exits the power down routine.

FIGS. 13–18 show the general shape of the pump housing 20 which has also been described with reference to FIG. 1. Note though that the details of console 42 and connectors 22A and 22B have been omitted in FIG. 14 to focus attention on the shape of housing 20. Screws 201–204 (shown in FIG. 15) are common screws which secure front plate 26 to rear plate 27. Of course, other conventional connectors could be used instead. Spacers 205–208 on the underside of housing 20 allow for level placement of the pump unit 501 on a flat surface. Spacers 210 and 211, along with spacers 205 and 206, ensure free flow of air into the pump unit's air intake 215, even when the unit is mounted snugly against a foot board 600 (FIG. 18) of a hospital bed.

Figure 18:
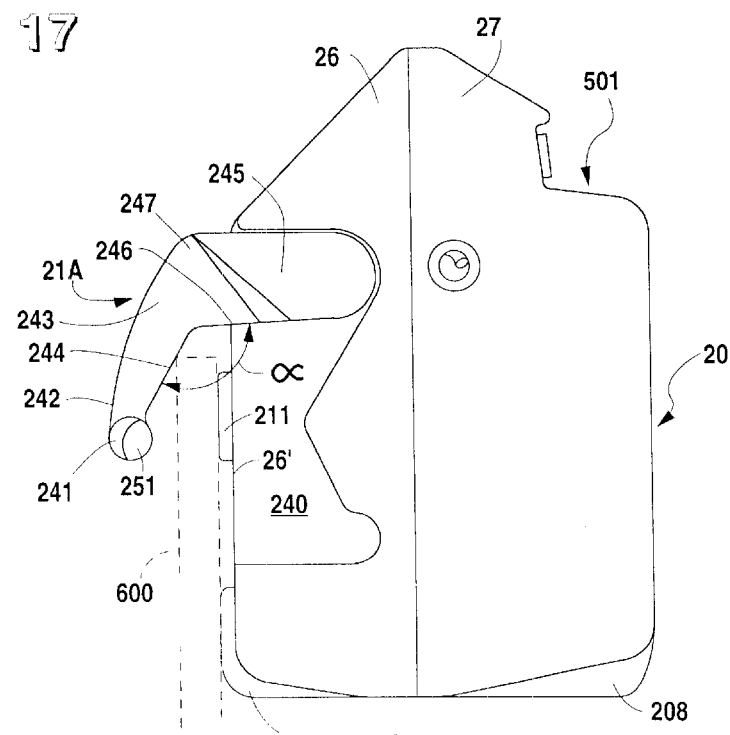
FIG. 18 shows the left side elevation view of FIG. 17, except that the retractable mounting hooks 21 are in their fully extended position in FIG. 18, as also pictured in FIG. 1.
Figure 19:
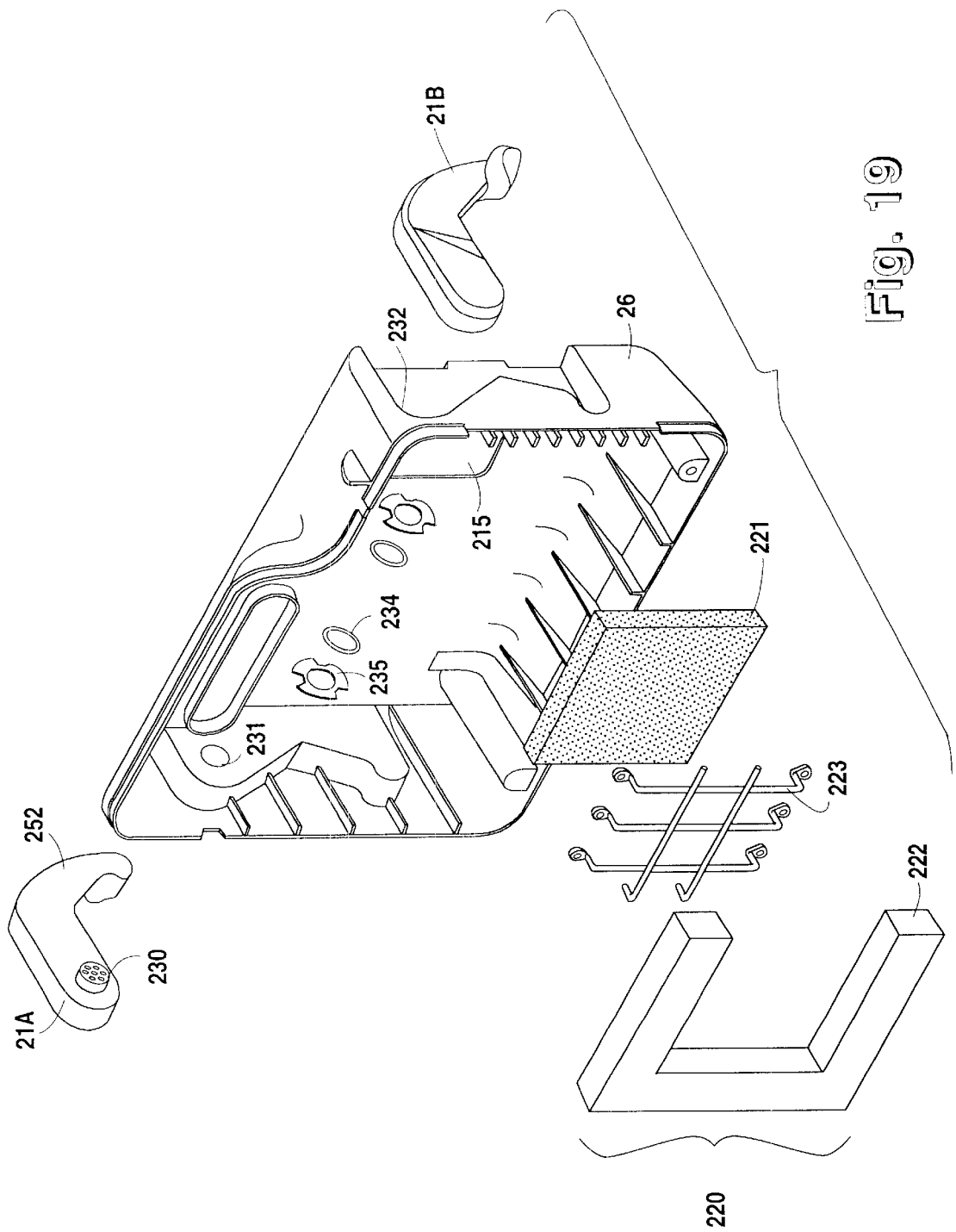
FIG. 19 shows an exploded view of the rear portion of pump 20.

Assembly of the back plate 26 is best understood with reference to FIG. 19. As shown therein, air intake filter assembly 220 is mounted to the inside surface of back plate 26. Assembly 220 basically includes a primary filter 221 and a secondary filter 222 together with mounting bracket 223. Primary filter 221 is fairly porous to allow free intake of air while secondary filter 222 is positioned to surround the internally-exposed edges of primary filter 221 to ensure that all intake air is adequately filtered even if it circumvents primary filter 221. Bracket 223 is rigidly secured to the back plate 26 in a manner that cages primary filter 221 in place over intake 215. Secondary filter 222 is glued in place afterwards. The location of intake 215 is ideal as it is partially shielded from liquids and foreign objects when housing 20 is operatively mounted on a foot board 600 of a hospital bed. Such liquids and foreign objects, naturally, might otherwise impede the operation of unit 501, much less the free flow of air into inlet 215. Spacers 210 and 211 preferably provide a ³⁄₁₆ inch separation between the foot board 600 (shown in phantom line in FIG. 18) and intake 215 to ensure free air flow therein.

Figure 17:
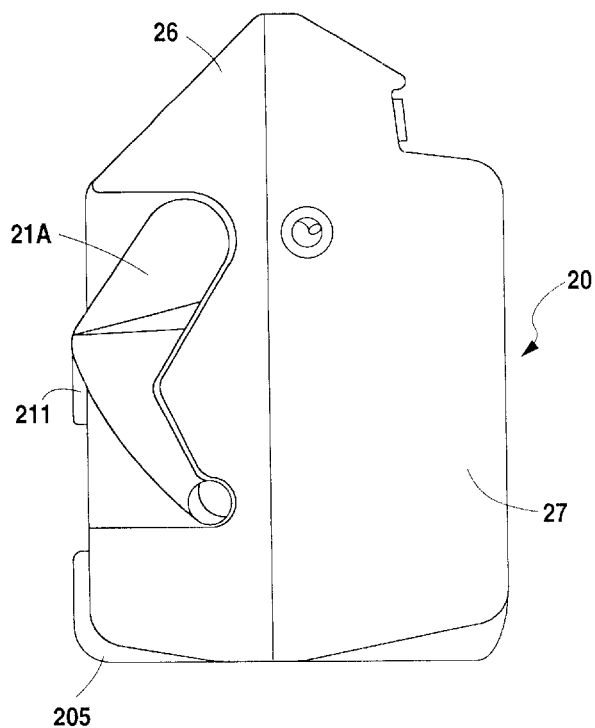
FIG. 17 shows a left side elevation view of the pump housing 20, with retractable mounting hooks 21 in their fully retracted position as in FIGS. 13–16.

Retractable mounting hooks 21A and 21B are shaped as shown best in FIGS. 17–19. Hooks 21A and 21B are similar to each other and are symmetrically mounted in a pivotal manner to plate 26. The pivotal mounting is best shown in FIG. 19, with reference to hook 21A. As shown therein, hook 21A is pivotally mounted by means of an integral shank 230 that fits snugly through a hole 231 in an irregular socket 240 (numbered in FIG. 18) formed in plate 26. Hole 231 is substantially coaxial with hole 232 so that the hooks 21A & B pivot in parallel planes that are perpendicular to back plate 26 in the preferred embodiment. Once inserted through hole 231, shank 230 is pivotally secured therein by a locking push ring 234. A spring washer 235 is positioned on the shank 230 to spring bias the shank through the hole in the same manner as a Bellview washer. Although not clear in FIG. 19, portions of spring washer 235 are bent in a manner that provides such a spring action. The locking push ring 234 is appropriately sized and flared around its inner circumference in a conventional manner so that it can be pushed onto shank 231 but the flare prevents it from sliding back off the shank 231. Thus ring 234 provides a permanent pivotal connection for hook 21A.

Although not shown very well in the drawings, it is preferred that slight tongue and groove reliefs are provided on the mating surfaces between the hook 21A and plate 26 so that hook 21A tends to click into place in either its fully retracted or fully extended positions. The spring bias of washer 235 helps provide such a clicking action as it tends to retain hook 21A in its clicked position. FIG. 17 shows hook 21A in its fully retracted position, and FIG. 18 shows hook 21B in its fully extended position. Socket 240 is shaped to neatly receive hook 21A when it travels from its fully extended to its fully retracted positions.

The innovative shape of hook 21A is best appreciated with reference to FIG. 18. Progressing from shank 230 outward, portions of hook 21A are referred to as shoulder 245, elbow 247, forearm 243, and knob 241, all formed as an integral member which is generally progressively thinner toward knob 241. The inner face 252 of hook 21A approximates a planar surface (except for the protrusion of shank 230) so that hook 21A pivots freely into socket 240. Knob 241, on the other hand, protrudes outward in a direction opposite shank 230 to roughly twice the thickness of forearm 243. Knob 241 is cylindrical in shape with its leading outer corner truncated and rounded to form a smooth finger pad 251. Finger pad 251 enables manual pivoting of hook 21A from its fully retracted to its fully extended position. The point of juncture between knob 241 and forearm 243 is referred to as wrist 242.

The forwardmost edges 244 and 246 of forearm 243 and shoulder 245 are substantially planar sections which are parallel to axis 250 of shank 230 and, therefore, appear linear in FIGS. 17 and 18. Although fillets are provided at wrist 242 to reduce stress concentrations, the plane of edge 244 is roughly perpendicular to the cylindrical surface of knob 241. Knob 241 thus forms a protruding lip at the distal end of forearm 243, and this lip helps retain pump unit 501 on foot board 600 even if it is knocked outward from the foot board.

Because standard foot boards range from ½ to 1½ inches in width, it may also be helpful to consider some of the dimensions of hook 21A. The pivot axis 250 for the hook 21A is preferably as high as possible on housing 20 and should be at least high enough to ensure the center of gravity of pump unit 501 is lower than the center of distal knob 241, to help ensure against tipping. To accommodate a range of foot board sizes, the distance between the crease 248 of elbow 247 and the planar surface 26' of back plate 26 (when hook 21A is fully extended) is ⅞ inches, thereby snugly receiving the smallest of standard foot boards while leaving the ⅜ inch space provided by spacers 210 & 211. At the opposite extreme, the forwardmost edge of knob 241 is 1⅞ inches from surface 26' (when fully extended), thereby snugly accommodating the widest of standard hospital foot boards. Moreover, for any foot boards in the range of standard sizes, the weight of pump unit 501 tends to pull surface 26' downward and thus closer to foot board 600 due to the constant slope of edge 244, until each of spacers 210 & 211 engage the foot board 600. Referring to angle alpha (FIG. 18) the slope of edge 244 is such that alpha is an obtuse angle less than 135 degrees. Preferably, alpha is roughly 115 degrees. With such construction, housing 20 is adapted for snug, secure and neat mounting on hospital bed foot boards 600 in the full range of standard sizes.

Although the present invention has been described in terms of the foregoing preferred embodiments, such embodiments are merely exemplary of the present invention. As will be apparent to those of ordinary skill in the art, many other alternatives, equivalents, modifications, objects, substitutions, variations and the like, of varying degrees, will fall within the scope of the present invention. For instance, the number, specifications and locations of various components or the sequence, number, and complexity of various steps can generally be modified to some degree while still serving substantially the same purposes of the present invention. As a particular example, air control board 50 and control board 41 may be combined into a single integrated circuit board to minimize costs and space constraints, as Applicant has done in alternative embodiments. Accordingly, nothing in the foregoing detailed descriptions limits the scope of the present invention in any respect, but rather that scope is defined instead only by the claims which follow, construed as broadly as possible.

I claim:

1. A medical apparatus for affecting blood circulation comprising:
    a wrap comprising an inflatable bladder for applying pressure to a patient's extremity when inflated;
    a pressure source for inflating the bladder in said wrap;
    a pressure sensor for sensing the pressure applied to the patient's extremity and converting the sensed amount into a signal; and
    a controller for receiving the signal from said pressure sensor to control the pressure applied to the patient's extremity by said pressure source in cyclic inflation and deflation cycles, said controller being adapted for gradually increasing the pressure applied by said wrap over a series of successive inflation/deflation cycles.

2. The apparatus of claim 1 additionally comprising a line in fluid communication with said pressure source and the bladder in said wrap having at least one restrictor therein for restricting the flow of pressure to said pressure sensor.

3. The apparatus of claim 1 wherein the signal from said pressure sensor includes an analog voltage signal, and said pressure sensor further comprises an analog to digital conversion means for converting the analog voltage signal into a digital signal.

4. The apparatus of claim 1 wherein said control means comprises micro-controller and a plurality of solenoid valves controlled by said micro-controller to adjust the amount of pressure applied by said pressure source to said wrap.

5. The apparatus of claim 4 wherein said micro-controller reads the signal from said pressure sensor and opens and closes the solenoid valves in response to the read signal.

6. The apparatus of claim 4 wherein said controller further comprises an error detection means for determining when pressure applied by said pressure source is either too high or too low.

7. The apparatus of claim 4 wherein said controller further comprises an operator console having programmable keys to enter user settings and memory means for storing said user settings to be processed by said micro-controller.

8. The apparatus of claim 7 wherein said operator console further comprises a liquid crystal display.

9. The apparatus of claim 7 wherein said memory means comprises an electronically erasable programmable read only memory.

10. A medical apparatus for cyclically applying pressure to a foot comprising:
    a foot wrap formed from two sheets of flexible fabric having an inflatable bladder therein;
    a connector opening into the inflatable bladder for connecting to a source of pressurized fluid;
    said foot wrap having a first tab for releasably securing said foot wrap to a human foot about the arch and a second tab for releasably securing said foot wrap about the heel, the second tab being generally perpendicular to the first tab;
    a source for supplying pressurized fluid to said inflatable bladder;
    a sensor for sensing the pressure in said inflatable bladder; and
    a controller in communication with said pressure sensor for adjusting the amount of pressure supplied to said bladder by said source based on pressures sensed by said pressure sensor.

11. The medical apparatus of claim 10 further comprising:
    housing for releasably mounting said source on a foot board of a standard hospital bed, said housing comprising a pair of opposite mounting hooks having sloping surfaces for biasing the source toward said foot board and having knobs at the distal ends thereof for helping retain the hooks on the foot board; and
    said hooks having a horizontal bearing surface for engaging the top of foot boards having smaller widths.

12. A medical apparatus for affecting the circulation of a patient's body fluid comprising:
    a wrap having an inflatable bladder for applying pressure to a patient's extremity when inflated;
    a source for supplying gas to said wrap;
    an expansion chamber in fluid communication with said gas source;
    a line in fluid communication with said expansion chamber and the bladder in said wrap;
    a pressure sensing means including a pressure sensor connected to said line for sensing the amount of gas being supplied by said gas source upon opening a valve and converting the sensed pressure into a signal for controlling the valve; and
    a controller operatively connected with said pressure sensing means to receive the signal therefrom to control the valve to adjust the amount of gas being supplied to the bladder in said wrap by said gas source in cyclic inflation and deflation cycles, said controller being adapted for gradually increasing the pressure applied by said wrap over a series of successive inflation/deflation cycles.

13. A method for affecting the circulation of body fluid in the extremity of a patient comprising the steps of:

applying a wrap to a patient's extremity, the wrap comprising an inflatable bladder for applying pressure to the patient's extremity;

supplying pressure to the wrap;

approximating the pressure in the bladder by delivering the pressure to the bladder through an expansion reservoir;

sensing the amount of pressure being supplied by the pressure source in the expansion reservoir; and converting the sensed pressure in the expansion reservoir into a signal for controlling the pressure supplied to the wrap.

14. A method for affecting the circulation of body fluid in a patient comprising the steps of:

applying a wrap comprising an inflatable bladder for applying pressure to the body of a patient;

supplying pressure to the wrap in cycles of inflation and deflation of the bladder; and sensing the pressure in an accumulator tank in fluid communication with the bladder upon opening of a valve in fluid communication with the bladder to deflate the bladder during each inflation/deflation cycle thereby verifying the decrease in the pressure during deflation of the bladder by sensing a decrease in the pressure in the accumulator tank.

* * * * *

UNITED STATES PATENT AND TRADEMARK OFFICE
CERTIFICATE OF CORRECTION

PATENT NO. : 6,468,237 B1
DATED : October 22, 2002
INVENTOR(S) : Cesar Z. Lina

It is certified that error appears in the above-identified patent and that said Letters Patent is hereby corrected as shown below:

Title page,
Item [56], References Cited, the entire section should be deleted and replaced with the following:

U.S. PATENT DOCUMENTS

| | | | | |
|---|---|---|---|---|
| 1,608,239 | A | | 11/1926 | Rosett |
| 2,531,074 | A | | 11/1950 | Miller |
| 2,834,340 | A | | 5/1958 | Walter |
| 2,880,721 | A | | 4/1959 | Corcoran |
| 3,171,410 | A | | 3/2/1965 | Towle, Jr. et al. |
| 3,292,613 | A | | 12/1966 | MacLeod |
| 3,303,841 | A | | 2/1967 | Dennis |
| 3,391,692 | A | | 11/1973 | Spielberg |
| 3,403,673 | A | | 10/1968 | MacLeod |
| 3,442,270 | A | | 5/1969 | Steinman |
| 3,454,010 | A | | 7/1969 | Lilligren et al. |
| 3,618,595 | A | * | 11/1971 | Stahmer ............... 128/25 R |
| 3,654,919 | A | | 4/1972 | Birtwell |
| 3,659,593 | A | | 5/1972 | Vail |
| 3,701,349 | A | | 10/1972 | Larson |
| 3,773,036 | A | | 11/1973 | Weyer |
| 3,811,431 | A | * | 5/1974 | Apstein ................... 128/64 |
| 3,824,992 | A | | 7/1974 | Nicholson, et al. |
| 3,856,008 | A | | 12/1974 | Fowler, et al. |
| 3,878,839 | A | | 4/1975 | Norton et al. |
| 3,888,242 | A | | 6/1975 | Harris et al. |
| 3,901,221 | A | | 8/1975 | Nicholson, et al. |
| 3,901,225 | A | | 8/1975 | Sconce |
| 3,908,642 | A | | 9/1975 | Vinmont |
| 3,920,006 | A | | 11/1975 | Ladipus |
| 3,933,150 | A | | 1/1976 | Kaplan, et al. |
| 3,942,518 | A | * | 3/1976 | Tenteris, et al. ..... 128/24 R |
| 4,013,069 | A | | 3/1977 | Hasty |
| 4,029,087 | A | | 6/1977 | Dye et al. |
| 4,030,488 | A | | 6/1977 | Hasty |
| 4,033,337 | A | | 7/1977 | Raczkowski |
| 4,077,402 | A | | 3/1978 | Benjamin, Jr. et al. |
| 4,081,150 | A | | 3/1978 | Tyson |
| 4,091,804 | A | | 5/1978 | Hasty |
| 4,106,002 | A | * | 8/1978 | Hogue, Jr. .............. 606/202 |
| 4,156,425 | A | | 5/1979 | Arkans |

UNITED STATES PATENT AND TRADEMARK OFFICE
CERTIFICATE OF CORRECTION

PATENT NO. : 6,468,237 B1
DATED : October 22, 2002
INVENTOR(S) : Cesar Z. Lina

It is certified that error appears in the above-identified patent and that said Letters Patent is hereby corrected as shown below:

Title page (cont'd),

| | | | | |
|---|---|---|---|---|
| 4,202,325 | A | | 5/1980 | Villari et al. |
| 4,231,355 | A | | 11/1980 | Hara |
| 4,343,302 | A | | 8/1982 | Dillon |
| 4,413,620 | A | | 11/1983 | Tucker |
| 4,419,988 | A | | 12/1983 | Mummert |
| 4,502,470 | A | | 3/1985 | Kiser, et al. |
| 4,590,925 | A | | 5/1986 | Dillon |
| 4,614,180 | A | | 9/1986 | Gardner, et al. |
| 4,624,244 | A | * | 11/1986 | Taheri ............... 128/24 R |
| 4,696,289 | A | * | 9/1987 | Gardner et al. ......... 128/64 |
| 4,738,249 | A | | 4/1988 | Linman et al. |
| 4,747,398 | A | | 5/1988 | Wright |
| 4,753,226 | A | | 6/1988 | Zheng et al. |
| 4,793,328 | A | * | 12/1988 | Kolstedt et al. ........ 128/24R |
| 4,805,601 | A | | 2/1989 | Eischen, Sr. |
| 4,841,956 | A | | 6/1989 | Gardner, et al. |
| 4,846,160 | A | | 7/1989 | Gardner, et al. |
| 4,865,020 | A | | 9/1989 | Bullard |
| 4,941,458 | A | | 7/1990 | Taheri |
| 4,945,905 | A | | 8/1990 | Dye |
| 4,947,834 | A | | 8/1990 | Kartheus et al. |
| 4,971,044 | A | | 11/1990 | Dye |
| 4,989,589 | A | | 2/1991 | Pekanmaki et al. |
| 5,000,164 | A | | 3/1991 | Cooper |
| 5,007,411 | A | | 4/1991 | Dye |
| 5,027,797 | A | * | 7/1991 | Bullard ................. 601/152 |
| 5,031,604 | A | * | 7/1991 | Dye ........................ 128/64 |
| 5,052,128 | A | | 10/1991 | Lonardo |
| 5,052,377 | A | * | 10/1991 | Frajdenrajch ........... 128/64 |
| 5,063,910 | A | * | 11/1991 | Cartier ................. 128/24R |
| 5,090,404 | A | * | 2/1992 | Kallassy .............. 602/23 X |
| 5,113,877 | A | | 5/1992 | Johnson, Jr. et al. |

FOREIGN PATENT DOCUMENTS

| | | |
|---|---|---|
| 0514204A1 | 11/1992 | European Pat. Off. |
| 2141938A | 1/1985 | United Kingdom |
| 836549 | 8/1951 | Germany |
| 837759 | 8/1951 | Germany |
| 2433794 | 1/1976 | Germany |
| SU574213 | 10/1977 | Russia |
| SU852328 | 8/1981 | Russia |
| 166270 | 2/1959 | Sweden |
| 2390156 | 8/1978 | France |
| 2716137 | 11/1994 | France |
| 47-009291 | 5/1972 | Japan |

UNITED STATES PATENT AND TRADEMARK OFFICE
CERTIFICATE OF CORRECTION

PATENT NO. : 6,468,237 B1
DATED : October 22, 2002
INVENTOR(S) : Cesar Z. Lina

It is certified that error appears in the above-identified patent and that said Letters Patent is hereby corrected as shown below:

Title page (cont'd),

```
47-010392   5/1972   Japan
48-020636   5/1973   Japan
49-027091   5/1974   Japan
52-117102   10/1977  Japan
54-086897   7/1979   Japan
55-000160   5/1980   Japan
```

OTHER PUBLICATIONS

Landis, E.M. and Gibbon, J.H., Jr., "The Effects of Alternate Suction and Pressure on Blood Flow to the Lower Extremities," Journal of Clinical Investigation, , Vol. 12, pp. 925-961, 1933.

McCarthy, H.H., et al., "A New Method of Preventing the Fatal Embolus; Preliminary Report" Surgery, pp. 891-896, June, 1949.

McCarthy, H.H., et al., "Thromboembolism and Pulmonary Emboli", A.M.A. Archives of Surgery, vol. 75, pp. 493-499, October, 1957.

Loane, R.A., "Effect of Rhythmically Inflating a Pneumatic Cuff at the Ankle on Blood Flow in the Foot," Journal of Applied Physiology, Vol. 14 (3), pp. 411-413, 1959.

Parrott, J.C.W., published master's thesis entitled The Effect of a Mechanical Venous Pump on the Circulation in the Feet in the Presence of Arterial Obstruction, Department of Physiology, University of Manitoba, October, 1972.

Gaskell, P. & Parrott, J., "The Effect of a Mechanical Venous Pump on the Circulation of the Feet in the Presence of Arterial Obstruction," Surgery, Gynecology & Obstetrics, Vol. 146, pp. 583-592, April, 1978.

Collard, J.J., Kuiper, J.P. and Brakkee, A.J.M., "Action De La Pompe Veineuse Du Pied Chez Des Patients Atteints D'Acro-Angiodermatitis," Phlebologie, 31(3), 249-256 (1978).

Anonymous, "Physical methods of prophylaxis against venous thrombosis," British Medical Journal, 282, 1341-1342 (1981).

Mahrxuha, et al., "Application of Vibrostimulating Footwear In The Complicated Treatment of Patients Suffering From Brain Insult," Journal of Neuropathology and Psychiatry, Vol. 8, pp. 26-29, 1982.

Hartman, J.T., et al., "Cyclic Compression of the Lower Limb in Prevention of Deep Venous Thrombosis," Journal of Bone & Joint Surgery, Vol. 64A, pp. 1059-1062, Sept. 1982.

UNITED STATES PATENT AND TRADEMARK OFFICE
CERTIFICATE OF CORRECTION

PATENT NO. : 6,468,237 B1
DATED : October 22, 2002
INVENTOR(S) : Cesar Z. Lina

It is certified that error appears in the above-identified patent and that said Letters Patent is hereby corrected as shown below:

Title page (cont'd),

Gardner, A.M.N. & Fox, R.H., "The Venous Pump of the Human Foot -- Preliminary report," Bristol Medico Chirurgical Journal, pp. 109-112, July, 1983.

MacEachern, A.G., et al., "The Venous Foot Pump," presented at the British Orthopaedic Association, Autumn Meeting, Leeds/Harrogate, 18-20 September, 1985.

Dillon, R., "Treatment of Resistant Venous Stasis Ulcers and Dermatitis with the End-Diastolic Pneumatic Compression Boot," Journal of Vascular Diseases, pp. 47-55, January, 1986.

Becket, C. & Wall, M., "The Venous Pump Of The Foot," Nursing Times, Vol. 84, No. 19, pp. 45-47, 1988.

Binns, M. and Pho, R.W.H., "Anatomy of the 'venous foot pump'," Injury 19, 443-445 (1988).

Gardner, A.M.N. & Fox, R.H., The Return of Blood To The Heart; venous pumps in health and disease, John Libbey & Company Ltd., 1989.

Fox, R.H. and Gardner, A.M.N., "Plantar Venous Pump," Injury 21, 129-130 (1990).

Gardner, et al., "Reduction of Post-Tramatic Swelling And Compartment Pressure By Impulse Compression of The Foot,"

The Journal of Bone and Joint Surgery, Vol. 72B, No. 5, pp. 810-815, 1990.

"Prevention of Venous Thrombosis and Pulmonary Embolism," The National Institutes of Health Consensus Development Conference Statement, Vol. 6, No. 2 (undated).

"A-V Impulse System," Novamedix, Ltd., 1988.

"Proven Prophylaxis with the Intermittent Compression Arthrombic Pump," Jobst Institute, Inc., 1987.

"A Lifetime of Innovative Treatment; Lympha Press," Camp International, Inc. (undated).

"Introducing Extremity Pumps That Take the Pressure Off By..." Jobst Institute, Inc., 1988.

"To Prevent Deep Venous Thrombosis," Venodyne Division of Advanced Instruments, Inc. (undated).

"Intermittent Compression. Naturally," Chattanooga Corp. (undated).

"Flowpress; Home Care Compression Systems," Huntleigh Technology, Inc. (undated).

"Flowtron DVT," Huntleigh Technology, Inc. (undated).

UNITED STATES PATENT AND TRADEMARK OFFICE
CERTIFICATE OF CORRECTION

PATENT NO. : 6,468,237 B1
DATED : October 22, 2002
INVENTOR(S) : Cesar Z. Lina

It is certified that error appears in the above-identified patent and that said Letters Patent is hereby corrected as shown below:

Title page (cont'd),

"Flowpulse," Huntleigh Technology, Medical Division (undated).
"Wright Linear Pump" (undated).
"Grossan Hydropulse" (undated).
"CONAIR Health Care Products" (undated).
"MASSATOR-PEDIO" (undated).
"Norelco Massager and Heat Belt" (undated).
"P.A.S. Pulsatile Anti-Embolism System" (undated).
"The Therapy Proven With Every Footstep" – Plexipulse™ brochure NuTech—A KCI Company (date unknown, but brochure bears 1991 copyright date).

Column 25,
Line 60, replace the words "control means" with the word -- controller --.
Line 61, insert the article -- a -- between the words "comprises" and "micro-controller."

Signed and Sealed this

Seventeenth Day of August, 2004

JON W. DUDAS
*Acting Director of the United States Patent and Trademark Office*